United States Patent
Eibl et al.

(10) Patent No.: US 10,912,534 B2
(45) Date of Patent: Feb. 9, 2021

(54) SYSTEMS AND METHODS FOR AUTOMATED FLUID RESPONSE MEASUREMENT

(71) Applicant: 1929803 ONTARIO CORP., Sudbury (CA)

(72) Inventors: Joseph Eibl, Sudbury (CA); Jon-Emile Kenny, New York, NY (US); Paul Magnin, Boston, MA (US); Andrew Eibl, Sudbury (CA)

(73) Assignee: 1929803 Ontario Corp., Sudbury (CA)

( * ) Notice: Subject to any disclaimer, the term of this patent is extended or adjusted under 35 U.S.C. 154(b) by 735 days.

(21) Appl. No.: 15/619,202

(22) Filed: Jun. 9, 2017

(65) Prior Publication Data

US 2017/0332995 A1   Nov. 23, 2017

Related U.S. Application Data

(63) Continuation-in-part of application No. PCT/CA2016/051451, filed on Dec. 9, 2016.
(Continued)

(51) Int. Cl.
  *A61B 8/06*   (2006.01)
  *A61B 8/00*   (2006.01)
  (Continued)

(52) U.S. Cl.
  CPC .............. *A61B 8/06* (2013.01); *A61B 5/026* (2013.01); *A61B 8/02* (2013.01); *A61B 8/0891* (2013.01);
  (Continued)

(58) Field of Classification Search
  CPC ....... A61B 8/06; A61B 8/4494; A61B 8/4227; A61B 8/0891; A61B 8/565; A61B 8/5223;
  (Continued)

(56) References Cited

U.S. PATENT DOCUMENTS 4,103,679 A    8/1978 Aronson
10,394,209 B2  8/2019 Goodon et al.
(Continued)

FOREIGN PATENT DOCUMENTS

CA    2950919 A1    1/2016
JP    S62501682 A   7/1987
(Continued)

OTHER PUBLICATIONS

European Patent Office, extended European search report for European Application No. 16871876.5; dated Sep. 20, 2019; 36 pages.
(Continued)

*Primary Examiner* — Peter Luong
(74) *Attorney, Agent, or Firm* — Perkins Cole LLP

(57) ABSTRACT

A device is provided for automatically assessing functional hemodynamic properties of a patient is provided, the device comprising: a housing; an ultrasound unit coupled to the housing and adapted for adducing ultrasonic waves into the patient at a vessel; a detector adapted to sense signals obtained as a result of adducing ultrasonic waves into the patient at the vessel and to record the; and a processor adapted for receiving the recorded signals as data and transforming the data for output at an interface. Other devices, systems, methods, and/or computer-readable media may be provided in relation to assessing functional hemodynamics of a patient.

20 Claims, 30 Drawing Sheets

Related U.S. Application Data

(60) Provisional application No. 62/265,682, filed on Dec. 10, 2015.

(51) Int. Cl.
  *A61B 8/08* (2006.01)
  *A61B 5/026* (2006.01)
  *A61B 8/02* (2006.01)
  *A61B 5/00* (2006.01)
  *A61H 31/00* (2006.01)

(52) U.S. Cl.
  CPC .......... *A61B 8/4227* (2013.01); *A61B 8/4236* (2013.01); *A61B 8/4427* (2013.01); *A61B 8/4477* (2013.01); *A61B 8/4494* (2013.01); *A61B 8/463* (2013.01); *A61B 8/465* (2013.01); *A61B 8/488* (2013.01); *A61B 8/5223* (2013.01); *A61B 8/565* (2013.01); *A61B 5/742* (2013.01); *A61B 8/065* (2013.01); *A61B 8/4405* (2013.01); *A61B 2560/0214* (2013.01); *A61B 2560/0462* (2013.01); *A61B 2560/0475* (2013.01); *A61H 31/004* (2013.01)

(58) Field of Classification Search
  CPC .......... A61B 8/488; A61B 8/465; A61B 8/463; A61B 8/4477; A61B 8/4427; A61B 8/02; A61B 8/4236; A61B 8/065; A61B 8/4405; A61B 8/00; A61B 8/56; A61B 8/5246; A61B 8/462; A61B 8/4455; A61B 8/4281; A61B 5/026; A61B 5/742; A61B 2560/0475; A61B 2560/0462; A61B 2560/0214; A61H 31/004; A61H 31/005; A61H 2201/5046; A61H 2201/501; A61H 2201/5097; A61H 2201/1688; A61H 2201/1609
  See application file for complete search history.

(56) References Cited

U.S. PATENT DOCUMENTS

| | | | |
|---|---|---|---|
| 2002/0042574 A1* | 4/2002 | Manor | A61B 8/06 600/454 |
| 2005/0156491 A1 | 7/2005 | Scott | |
| 2006/0206032 A1 | 9/2006 | Miele et al. | |
| 2006/0264756 A1 | 11/2006 | Lo et al. | |
| 2008/0208273 A1 | 8/2008 | Owen et al. | |
| 2010/0016725 A1 | 1/2010 | Thiele | |
| 2010/0049052 A1 | 2/2010 | Sharf et al. | |
| 2010/0076315 A1 | 3/2010 | Erkamp et al. | |
| 2011/0137173 A1 | 6/2011 | Lowe et al. | |
| 2012/0138533 A1 | 6/2012 | Curtis et al. | |
| 2012/0184854 A1 | 7/2012 | Raju et al. | |
| 2012/0277640 A1 | 11/2012 | Lewis, Jr. et al. | |
| 2012/0296216 A1 | 11/2012 | Sharf et al. | |
| 2014/0081144 A1 | 3/2014 | Moehring et al. | |
| 2014/0371594 A1 | 12/2014 | Flynn et al. | |
| 2015/0009782 A1 | 1/2015 | Engl et al. | |
| 2015/0135840 A1 | 5/2015 | Sato et al. | |
| 2015/0272513 A1* | 10/2015 | Tan | A61B 5/7282 600/505 |
| 2015/0289838 A1 | 10/2015 | Nichol et al. | |
| 2016/0206292 A1 | 7/2016 | Vezina | |
| 2017/0080255 A1 | 3/2017 | Law et al. | |
| 2017/0293277 A1 | 10/2017 | Goodon et al. | |
| 2017/0325328 A1 | 11/2017 | Isaac et al. | |
| 2018/0020982 A1 | 1/2018 | Elsherbini et al. | |
| 2018/0206819 A1 | 7/2018 | Saarinen et al. | |
| 2018/0353157 A1 | 12/2018 | Eibl et al. | |
| 2019/0021659 A1 | 1/2019 | Sajwan et al. | |
| 2019/0059848 A1 | 2/2019 | Owen et al. | |

FOREIGN PATENT DOCUMENTS

| | | |
|---|---|---|
| JP | 2002541899 A | 12/2002 |
| JP | 2004344564 A | 12/2004 |
| JP | 2008534071 A | 8/2008 |
| JP | 2008259850 A | 10/2008 |
| JP | 2009524467 A | 7/2009 |
| JP | 2012518454 A | 8/2012 |
| JP | 2014054580 A | 3/2014 |
| JP | 2015130520 A | 7/2015 |
| WO | 8604225 A1 | 7/1986 |
| WO | 0062677 A1 | 10/2000 |
| WO | WO2008042559 A2 | 4/2008 |
| WO | WO2009154298 A1 | 12/2009 |
| WO | WO2015074015 A1 | 5/2015 |
| WO | 2015181167 A1 | 12/2015 |

OTHER PUBLICATIONS

International Search Report and Written Opinion of International Application No. PCT/CA2017/050714; dated Mar. 2, 2018; 9 pages.
WIP, International Search Report and Written Opinion for PCT/CA2016/051451 dated Mar. 14, 2017.
Japanese Office Action in Japanese Application No. 2018-0530760; dated Oct. 26, 2020; 6 pages.

* cited by examiner

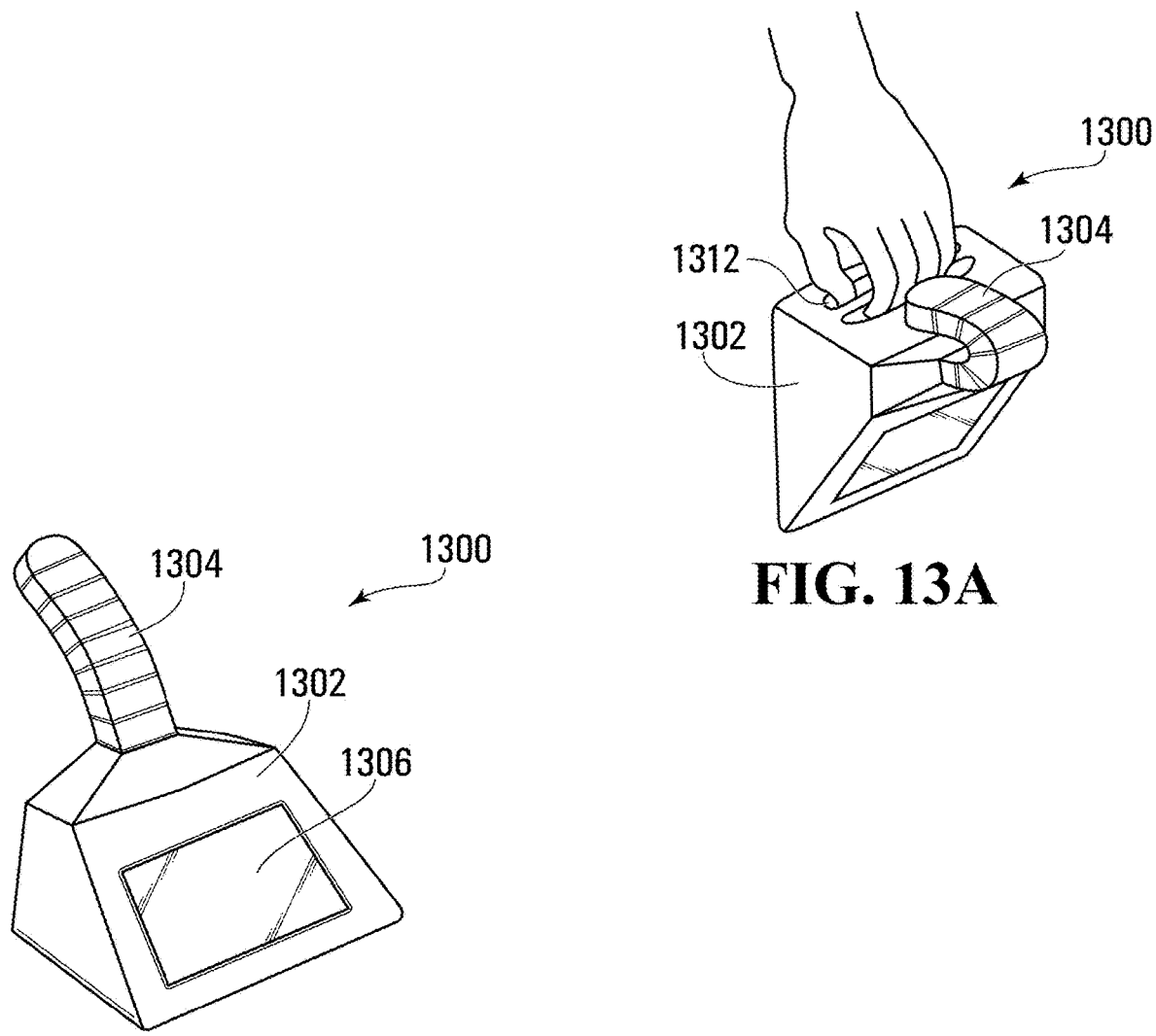
FIG. 13A
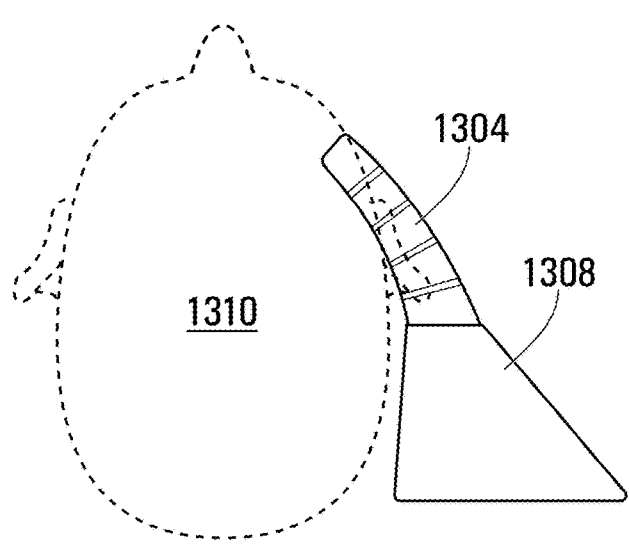
FIG. 13B
FIG. 13C

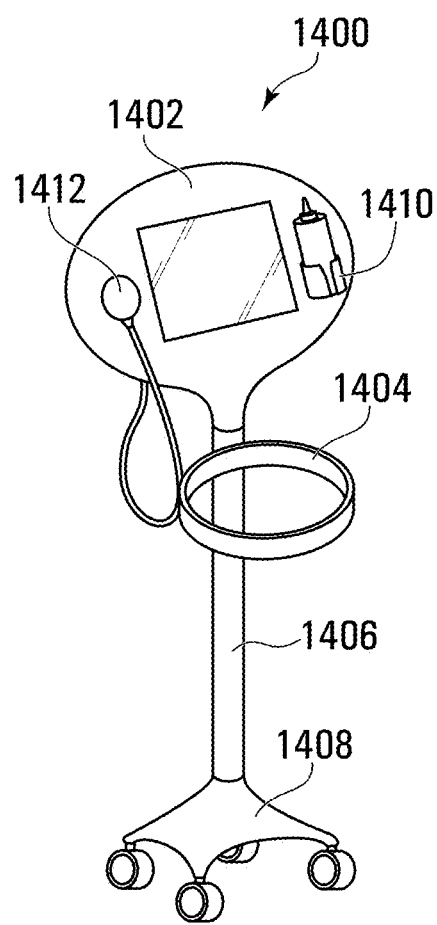
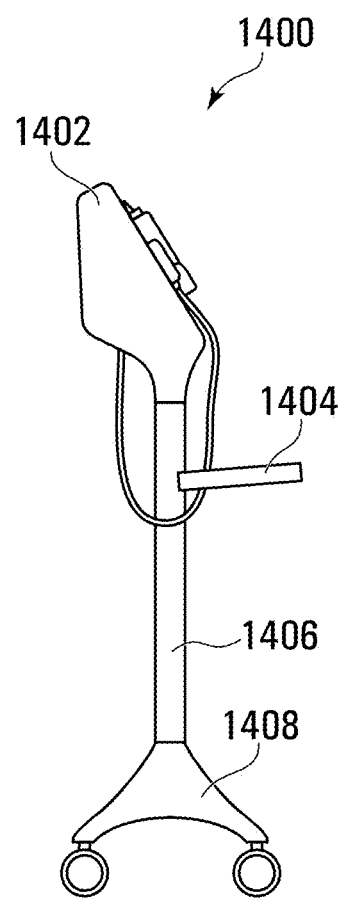
FIG. 14A  FIG. 14B

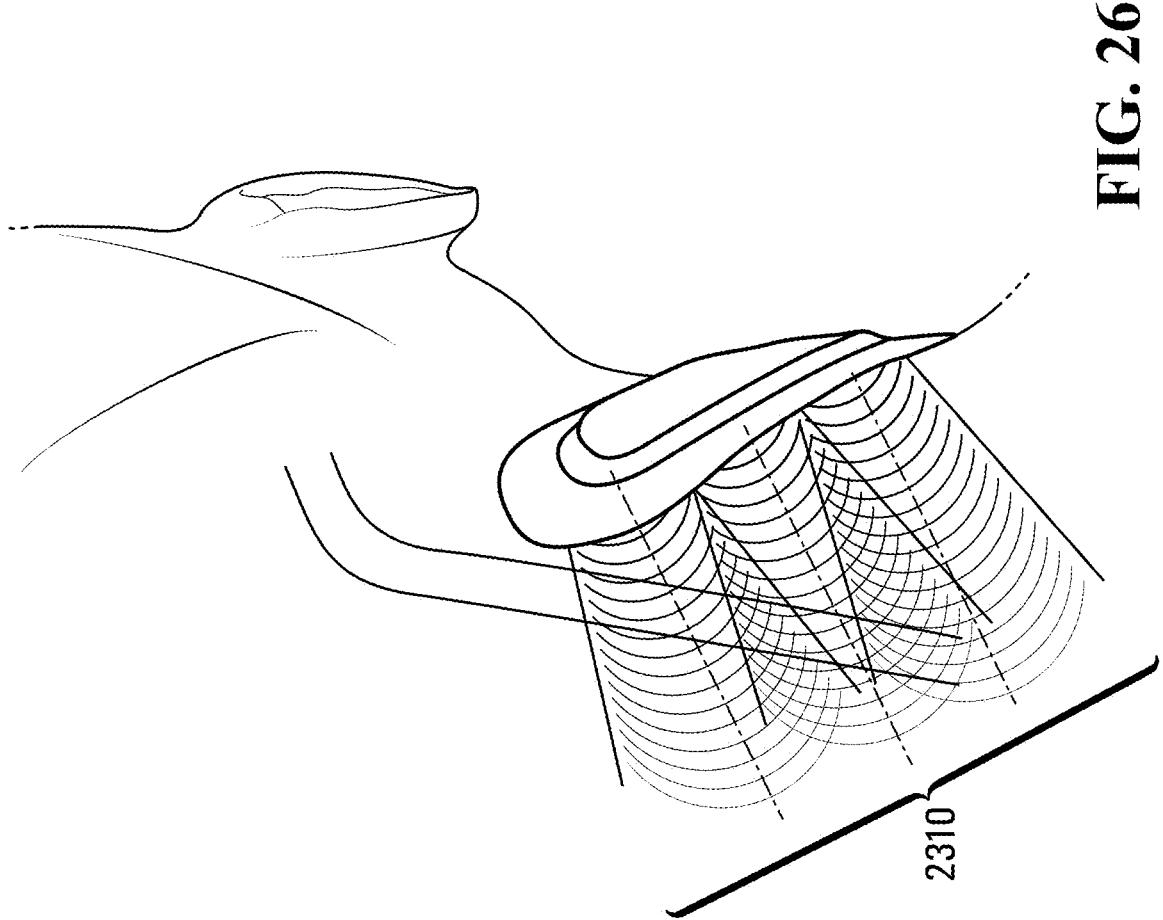
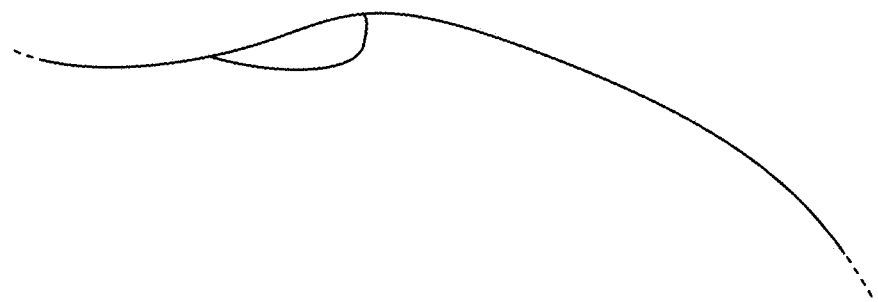
FIG. 26

SYSTEMS AND METHODS FOR AUTOMATED FLUID RESPONSE MEASUREMENT

CROSS REFERENCE

This application is a continuation-in-part of PCT Application No. PCT/CA2016/051451, entitled "SYSTEMS AND METHODS FOR AUTOMATED FLUID RESPONSE MEASUREMENT", filed 9 Dec. 2016, the PCT Application claiming priority to U.S. Application No. 62/265,682, entitled "SYSTEMS AND METHODS FOR AUTOMATED FLUID RESPONSE MEASUREMENT" filed 10 Dec. 2015.

FIELD

The present disclosure generally relates to the field of monitoring biological signals, and more particularly, hemodynamic monitoring of one or more patients.

INTRODUCTION

Innovative, affordable, and/or portable non-invasive hemodynamic monitoring devices may be desirable in the market. Such devices, for example, aid in the provisioning of care of various individuals, (e.g., the critically-ill) by providing functional hemodynamic assessments (which, in some embodiments, may be instantaneous or near instantaneous).

Non-invasiveness of monitoring/measurement is of importance as non-invasive devices do not require consideration of potential complications that would otherwise arise in conjunction with invasive interventions. For example, an invasive intervention could lead to infection, require additional surgical steps to be taken (which may not be possible when time is of the essence), require time for healing/tissue repair, among others. Further, non-invasive approaches, in the context of emergency situations, would have less requirements for sterilization, specialized skillsets and equipment.

The portability of a monitoring/measurement device is very desirable as the device may be transported to areas where it may be used (as opposed to having to have patients transported to come to where the device is located). However, portability implies that the device may need to be sufficiently small (not bulky), and light for ease of transportation, and further, may constrain available power delivery to the device due to a need for portability of power sources.

It is desirable to be able to assess functional hemodynamics in a variety of circumstances. Unstructured environments and the variance in experience and training among individuals responsible for assessing functional hemodynamics creates challenges. These challenges are exacerbated when a patient requires monitoring over a protracted period of time and many individuals are involved in assessing functional hemodynamics. There is a need for a device that will produce precise and repeatable measurements under these conditions.

SUMMARY

In accordance with an aspect, a portable non-invasive hemodynamic monitoring device is provided, the device including a housing configured for removable coupling to a body part of an individual, the body part including at least one vessel of interest; an ultrasound unit coupled to the housing and adapted for adducing ultrasonic waves into the at least one vessel of interest in a continuous beam, the ultrasound unit including: a plurality of transducer pairs adapted to continuously detect reflected ultrasonic waves derived at least in part from the produced ultrasonic waves directed at the at least one vessel of interest and oriented such that, in concert, the plurality of transducer pairs producing the ultrasonic waves at an angle of incidence between about 25 degrees to about 60 degrees in respect of a plane of fluid flow through the at least one vessel of interest; a processor configured to continuously extract hemodynamic parameters from one or more characteristics of the detected reflected ultrasonic waves in real-time or near real-time by applying a signal processing routine, and to store the extracted one or more hemodynamic parameters in a data storage; and a sensory output device adapted to provide feedback based at least on the extracted hemodynamic parameters, the sensory output device including at least one of (i) a graphical display and (ii) an auditory display; the orientation of plurality of transducer pairs maintained by the housing such that the plurality of transducer pairs are oriented to adduce the ultrasonic waves at substantially similar angles in respect of the plane of fluid flow through the at least one vessel of interest, the plurality of transducer pairs, in concert, adducing an unfocused ultrasonic curtain comprised of the ultrasonic waves that enables a plurality of redundant effective placement positions of the portable non-invasive hemodynamic monitoring device.

In accordance with an aspect, there is provided a portable non-invasive hemodynamic monitoring device comprising a housing configured for removable coupling to a body part of an individual, the body part including at least one vessel of interest; an ultrasound unit coupled to the housing and adapted for adducing ultrasonic waves into the at least one vessel of interest in a continuous beam, the ultrasound unit including: at least one transducer pair adapted to continuously detect reflected ultrasonic waves derived at least in part from the produced ultrasonic waves directed at the at least one vessel of interest and oriented such that, in concert, the at least one transducer pair produces the ultrasonic waves at an angle of incidence between about 25 degrees to about 60 degrees in respect of a plane of fluid flow through the at least one vessel of interest; a processor.

In accordance with another aspect, the processor is further configured to continuously extract hemodynamic parameters from one or more characteristics of the detected reflected ultrasonic waves in real-time or near real-time by applying a signal processing routine, and to store the extracted one or more hemodynamic parameters in a storage.

In accordance with another aspect, there is provided a sensory output device adapted to provide feedback on a quality of the extracted hemodynamic parameters, the sensory output device including at least one of (i) a graphical display and (ii) an auditory display. Wherein the orientation of the at least one transducer pair improves a probability of proper acoustic coupling between the ultrasound unit and the body part of the individual by enabling a plurality of redundant effective placement options of the housing on the body part of the individual, the plurality of redundant effective placement options reducing a required precision of placement of the device.

In accordance with another aspect, the signal processing routine includes processing the reflected ultrasonic waves according to a continuous wave Doppler ultrasound process.

In accordance with another aspect, the at least one transducer pair comprises a chain of transducer pairs.

In accordance with another aspect, the at least one transducer pair is at least one flexible polymer based transducer pair.

In accordance with another aspect, the at least one transducer pair is oriented in a saw tooth pattern, the saw tooth pattern causing the ultrasonic waves to be produced at the angle of incidence between about 25 degrees to about 60 degrees in respect of a plane of fluid flow through the at least one vessel of interest.

In accordance with another aspect, the housing includes a tension bandage that is utilized to provide the removable coupling between the housing and the body part of the individual, the tension bandage being tensioned such that a sufficient downward force is applied to the ultrasound unit.

In accordance with another aspect, the tension bandage is configured to maintain a substantially constant angle of incidence of the adduced ultrasonic waves relative to the at least one vessel of interest in order to enhance consistency of repeat measurements over a duration of time.

In accordance with another aspect, the sensory output device is configured to generate a sensory output indicating an effectiveness of placement of the ultrasound unit.

In accordance with another aspect, processor is further configured to detect an estimated return of spontaneous circulation (ROSC) event by measuring a difference between a first relative blood flow from a chest compression and a second relative blood flow from a heartbeat, and the sensory output device is configured to generate a sensory output indicating the occurrence of the detected estimated return of spontaneous circulation (ROSC) event and indicating that any chest compression activities should cease.

In accordance with another aspect, the housing includes at least one data communication device operable to transmit the extracted hemodynamic parameters from one or more characteristics of the detected reflected ultrasonic waves over a data network.

In accordance with another aspect, the data communication device transmits the extracted hemodynamic parameters from one or more characteristics of the detected reflected ultrasonic waves over the data network to an external computer system.

In accordance with another aspect, the housing includes at least one data transfer bus operable to transmit the extracted hemodynamic parameters from one or more characteristics of the detected reflected ultrasonic waves over a data connection.

In accordance with another aspect, the data transfer bus is operable to transmit the extracted hemodynamic parameters from one or more characteristics of the detected reflected ultrasonic waves over the data connection to one or more external connected devices.

In accordance with another aspect, the hemodynamic parameters include at least one of: a peak velocity of a Doppler shift detected in the at least one vessel of interest; a velocity-time integral of signal changes between heartbeats; and a ratio measured between a post-intervention velocity-time integral and a pre-intervention velocity-time integral.

In accordance with another aspect, the frequency of the ultrasonic waves is a frequency between about 3 MHz to about 12 MHz.

In accordance with another aspect, the frequency of the ultrasonic waves is a frequency is about 4 MHz.

In accordance with another aspect, the processor is configured to determine whether the individual is undergoing compensated shock by: continuously monitoring a ratio between a heart rate and a velocity-time integral of fluid flow through the at least one vessel of interest; entering a compensated shock alarm state when the ratio exceeds a predefined threshold; and producing an alarm signal when the compensated shock alarm state is entered.

In accordance with another aspect, the sensory output device is configured to transmit a signal when the processor determines that the individual is undergoing compensated shock.

In accordance with another aspect, the processor is further configured to: extract at least one first feature of interest from one or more characteristics of the detected reflected ultrasonic waves prior to an intervention event; extract at least one second feature of interest from one or more characteristics of the detected reflected ultrasonic waves subsequent to the intervention event; determine at least one post-intervention change value equivalent to the difference between the at least one first feature of interest and the at least one second feature of interest.

In accordance with another aspect, the intervention event is the administering of at least one medicament.

In accordance with another aspect, there is provided a device adapted for automatically assessing functional hemodynamics of a patient, the device comprising: a housing; an ultrasound unit coupled to the housing and adapted for adducing ultrasonic waves into the patient at a blood vessel; a detector adapted to sense signals obtained as a result of adducing ultrasonic waves into the patient at the blood vessel and to record the signals in the form of raw data; and a processor adapted for receiving the raw data and transforming the data for output at an interface.

In accordance with another aspect, the processor is further adapted to monitor functional hemodynamics (e.g., fluid dynamics) when the patient undertakes a fluid challenge activity.

In accordance with another aspect, the processor is further adapted to monitor functional hemodynamics both before and after the patient undertakes a fluid challenge activity.

In accordance with another aspect, the processor is further adapted to compare the data before the patient undertakes a fluid challenge activity and after the patient undertakes a fluid challenge activity to determine a change in velocity time integral of blood flow in the blood vessel.

In accordance with another aspect, the change in velocity time integral of blood flow in the blood vessel is tracked as a ratio of the velocity time integral before and following an intervention.

In accordance with another aspect, the processor is further adapted to provide the ratio and a notification for a clinician if the ratio is at least one of: 10% or greater, 15% or greater, or 20% or greater.

In accordance with another aspect, the ultrasound unit is provided as an ultrasonic probe separate from the housing and coupled operatively to the housing.

In accordance with another aspect, the device is provided in the form of a portable ultrasound unit.

In accordance with another aspect, the device is provided in the form of a cart mounted ultrasound unit, for example, a function specific transducer integrated into a cart/portable ultrasound can be provided in some embodiments.

In accordance with another aspect, the device is incorporated into a hand held ultrasound device.

In accordance with another aspect, the ultrasound unit is integrated into the housing.

In accordance with another aspect, the processor is adapted to perform the automated detection of blood flow in the blood vessel, the processor receiving the raw data from adducing the ultrasonic waves (e.g., in a continuous beam or a pulsed beam) into the patient at an angle opposing the blood flow in the blood vessel, obtaining a velocity time trace in relation to the blood flow, determining a velocity time integral, determining a cross-sectional surface area of the blood vessel, and utilizing the velocity time integral and the cross-sectional surface area of the blood vessel to establish the blood flow through the vessel across a period of time.

In accordance with another aspect, the processor is adapted to perform a validation protocol for identifying an optimal set of parameters for operation of the device.

In accordance with another aspect, the optimal set of parameters includes at least one of placement position, fixation type, selection of transducer pairs (e.g., one, some, or all) patch placement, and angle of incidence. In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 9A provides a top elevation view, FIG. 9B provides a perspective view, and FIG. 9C provides a side cross-sectional view, according to some embodiments.

FIG. 11A is a front perspective view of the embodiment; FIG. 11B is a rear perspective view of the embodiment; and FIG. 11C is a partial view of the embodiment.

FIGS. 12A-12B and FIGS. 13A-13C are illustrative of a small embodiment with integrated probe, according to some embodiments. FIG. 12A is a side view of this embodiment, and FIG. 12B is a perspective view of this embodiment. FIG. 13A is a perspective view of a second version of the embodiment with integrated probe being held at a handle. FIG. 13B is a perspective view of the second version; and FIG. 13C is a side view.

A cart embodiment is provided at FIGS. 14A and 14B; FIG. 14A is a front perspective view of a cart embodiment, and FIG. 14B is a side elevation view of the cart embodiment.

FIGS. 26 and 27 are illustrations of a device providing an unfocused curtain is provided, according to some embodiments.

DETAILED DESCRIPTION

Figure 1:
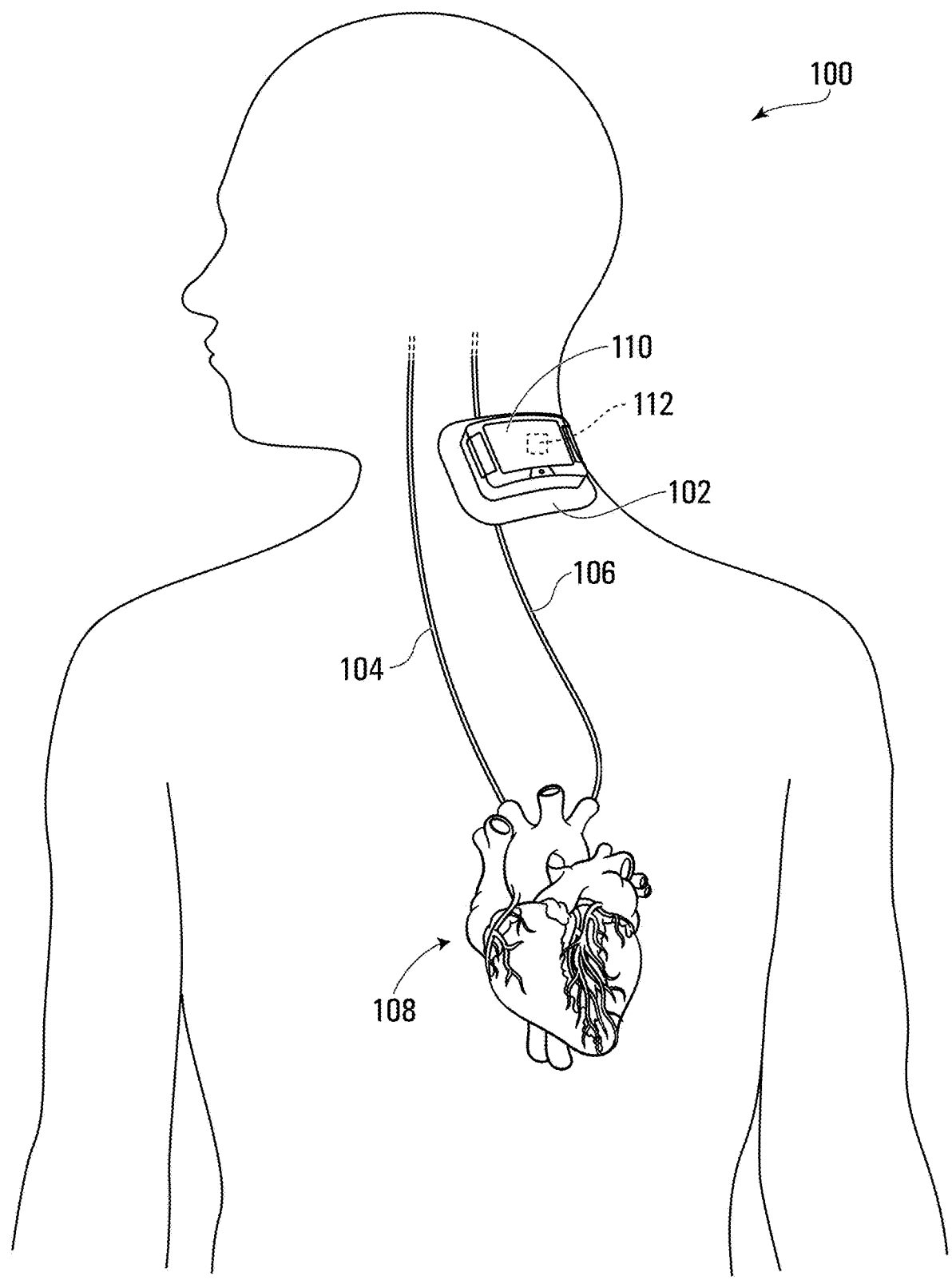
FIG. 1 is a perspective view of a device placed on the neck of a patient, according to some embodiments.

Embodiments of methods, systems, and apparatus are described through reference to the drawings.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Innovative, affordable, and/or portable non-invasive hemodynamic monitoring devices are desirable. Such devices, for example, aid in the provisioning of care of various individuals, (e.g., the critically-ill) by providing functional hemodynamic assessments (which, in some embodiments, may be instantaneous or near instantaneous).

There may be, however, various technical challenges in providing such a device, such as ensuring that readings are accurate, specific, and reliable within a tolerable performance range (e.g., accounting for the presence of noise, accounting for transient signals and/or aberrations); accounting for variations in physical dimensions and/or device placement, contact, and environment (e.g., differing neck sizes, contours, proximity of device, signal transfer characteristics); accounting for variations in procedures performed in conjunction with the device (e.g., differing fluid challenges).

The device may also encounter challenges as it relates to practical implementation, for example, the device may benefit from a level of intuitiveness and/or ease of use (e.g., portability, disposability, cost, understandable process, form factor), heat management, power (e.g., battery) management, adaptability to a variety of settings (including inside and outside of a hospital), etc.

Further, the device may benefit from a level of user-independent measurement repeatability, such that a patient, for whom many care-providers will be responsible, can monitor functional hemodynamics accurately over a protracted period of time. It may be desirable for such a device to contain access to memory and log sensor data over said protracted period of time.

A robust measurement device may be desirable, such that the device can provide real-time feedback during, for example, chest compressions associated with cardiopulmonary resuscitation (CPR), among other operations where comparing pre-/post-intervention measurements may also be desirable. Further still, it may be desirable to provide a device that adheres to the patient such that the care-provider's hands may be freed to perform other critical functions.

A device including an flexible ultrasound transducer is provided in some embodiments, the ultrasound transducer including aligned transducer pair(s) that are used to produce an unfocused sheet of ultrasound that can sample heterogeneous tissue (e.g., muscle, vessels, blood) to quantify forward and reverse blood flow. The device is non-invasive and is able to perform biological measurements without the need for insertion of other components (e.g., catheters). The non-invasive aspect is important in some embodiments as non-invasive approaches have a substantially lower risk of infection, do not require recovery time, and are more readily adapted for use by less skilled caregivers.

The transducer can be incorporated into a system for automatic flow monitoring and functional assessment without or with minimal user input, according to various embodiments. An example system may be a one-time use disposable portable ultrasound system that includes a tension bandage for secure coupling, that provides a cost-effective tool for use in emergency situations. The ultrasound system may be battery operated and configured for wireless communications (e.g., by cellular, WiFi, Bluetooth™). The system may have audio and graphic outputs included on the bandage, and in some embodiments, further signal processing is performed on an external device, such as a laptop, tablet or smart phone. Additional analytics may be mounted, such as components configured for determining hydration level.

The ultrasound transducer is designed for functioning without the user having to landmark and/or focus the ultrasound transducer on the vessel of interest, for example. by having wide array of continuous wave Doppler transducers as described in various embodiments. An unfocused curtain of ultrasonic signals generated from an array of non-coplanar elements (e.g., transducers all having the same fixed angle, angle may vary slightly due to device confirming to anatomy, or a matrix of fixed angle transducers) is provided such that redundant placement options are possible. For example, a plurality of transducers may be provided, and a highest signal-to-noise ratio pair may be selected. The device is developed to be relatively insensitive to placement on the patient (providing multiple placement and orientation options), so that it is quick and easy to deploy (e.g., many situations need extreme deploy-ability and ease of use, such as emergency and battlefield situations). Accordingly, reproducible measures (e.g., robust repeat sampling, reduced angle variability) and constant transducer angles are capable to be provided by design, rather than reliant on the user's skill level.

Some embodiments may be designed for hands-free usage, for example, a single operator in an intensive care unit may wish to utilize his/her hands for other functions. Other intervention may be effected while the device is in use, and ease of use and flexibility in application/placement is important as emergency caregivers may need to have their hands free to be able to administer the other intervention (e.g., fluid bolus therapy). The device of some embodiments is configured to track measurements pre- and post-intervention to track the efficacy of such intervention, using the fluid measurements as proxy for predicted efficacy (e.g., does there appear to be clinical improvement?).

The ultrasound transducer is distinguished from conventional imaging ultrasound in that it is adapted for practical usage in emergency situations where speed of use and placement are critical in delivering care. Conventional imaging ultrasound, while adapted for accuracy, typically require careful placement, good coupling, and use bulky diagnostic devices (for example, use alongside invasive diagnostic equipment, ECGs). Where careful placement is required, ultrasound system adjustments are typically needed. Further, where multiple ultrasonic transducers are utilized in conventional approaches, the multiple ultrasonic transducers are required to have beam intersection, presumably to aid in improving accuracy through mechanical focusing of beams. Rather than focusing a plurality of beams, some embodiments are configured to capture all or substantially all signal moving towards or away from the transducers in a large swath of tissue.

For example, some conventional approaches include the use of adhesive members with reference indicia for correct placement relative to anatomical landmarks, or complicated mechanisms where, for example, a plurality of transducer beams are required to intersect, among others. Such conventional approaches are not feasible or practical in the context of emergency care. Time is of the essence, and the ability to quickly deploy and obtain readings allows a primary caregiver a better chance of success.

By immobilizing (via adhesive patch with acoustic coupler on the neck) the transducer sets in a saw tooth orientation on an adhesive patch, a preferred embodiment is configured to enhance the reproducibility and comparability between repeat measures before and after an intervention (e.g., across multiple distinct events to extract hemodynamic parameters from the transducer pair(s)). In the preferred embodiment, the transducer sets and the saw tooth orientation are held to have a same angle of attack (e.g., beam angle) across each of the transducer sets in respect of a plane of fluid flow. This orientation allows the mechanism to emit signals that penetrate the tissue, and creates an "'unfocused ultrasound curtain" that provides for improved ease and flexibility of placement. For example, a caregiver may not necessarily have enough time to accurately determine placement, and the "unfocused ultrasound curtain" aids in establishing a redundancy of placement options such that the device or system is still operable despite suboptimal placement, providing a signal that is accurate enough for emergency care.

The system, in some confirmations, is able to monitor blood flow in two directions.

The ultrasound transducer may be incorporated into an overall system or device (e.g., a miniaturized singular device that operates as a one-piece bandage member that can be quickly applied prior to or during emergency care) that is configured to measure signals before, during, and/or potentially after an intervention, or combinations thereof. Differences in combinations of these signals can be used to identify, for example, the occurrence of events (e.g., return of spontaneous circulation), to determine characteristics of blood flow over a period of time (e.g., a velocity-time Integral), and/or to determine the efficacy of emergency intervention (e.g., an indication of feedback regarding success of CPR).

The device may be a standalone unit (e.g., having onboard displays or other interface elements) whereby auditory or visual displays are used to convey information regarding treatment. In other embodiments, the device is operable for use with downstream processors which receive raw or processed data sets from the device, and generate one or more healthcare insights based on the processing of the data sets, and such processors may be on-board, or on a separate device or in a distributed resources implementation (e.g., a cloud-based implementation). Some embodiments may offload processing to a connected smartphone/tablet/computer. In another embodiment, on-board processors may be utilized to perform further analysis and signal processing, for example, noise removal, artifact identification, signal shaping, metric extraction, among others.

FIG. 1 illustrates the device 102 placed on the neck of a patient, according to some embodiments. The device 102 is illustrated having various components and structural aspects, and it should be noted that the device 102 is provided merely as an example and embodiments may have different, alternate, the same, more, and/or less components and structural aspects.

The patients that may use this device 102, may, for example, be older in age and suffering from heart complications. The patients may be weak, may not be in a state of full awareness, and may be in danger of acute and critical illness. The device 102 may also be suitable for various other patient types.

Those patients who are alert are often in a stressful state. Though efficacy may be a significant factor, keeping the patient calm and comfortable is also an important factor.

A device 102 that seems to constrict or feel unnatural on the patient, such as a bulky or heavy neck mounted device 102, might serve to increase patient stress. A smaller device 102, or one with a detached probe, may be advantageous in this regard. Further a device 102 that is non-invasive is particularly desirable from a healthcare risk perspective.

The device 102 shown is configured for providing automated fluid response ultrasound (AFRU), and may, for example, be a body mounted device 102 that may be configured to incorporate a portable ultrasound unit to provide one or more assessments of a patient with consistency and/or accuracy. The device 102 may provide functional hemodynamic assessments, for example the device 102 may determine a patients fluid responsiveness (FR), in an automated fashion. In some embodiments, the local site on the patient is generally the neck area, such that the carotid artery is the vessel of interest and carotid flow is the target measurement. In some embodiments, the vessel of interest may be another vessel (e.g., brachial artery, femoral artery, etc.) and, as a result, the target measurement may change accordingly.

The device 102 may, for example, be used in the context of various uses, including an automated ultrasound in combination with a leg raise, the use of an automated ultrasound to give live readings during a fluid challenge (e.g., passive leg raise), etc. Further, the solution of the present disclosure may be non-intrusive, may be used by untrained users, may include methods by which certain target blood vessels are automatically differentiated from the other blood vessels, etc., and the device 102 may, in some embodiments, be used for multiple measurements where the device 102 may be fixed in place between measurements. For example, in some embodiments in order to differentiate target blood vessels from other blood vessels, forward and reverse flow signals may be classified as venous or arterial by application of a flow profile (e.g., pulsatile positive direction against non-pulsatile+opposite of positive direction). The transducer beam may be wide enough to capture the entirety of both arterial and venous signals at a particular monitored cross-section.

A user interface 110 may be integrated or operatively paired with the device and thus the device 102 may not require external supporting hardware. However, the device may, in some embodiments, be integrated with a data communication device 112, for example using the Bluetooth™ or W-Fi protocol. The data communication device 112 may be configured such that the device is capable of transmitting outputs to an external system (e.g., an external computer system) for processing, data storage, display, etc. The user interface 110 may be a visual display, a speaker, or another interface capable of communicating messages to a user of the device. In some embodiments, the device 102 may contain one or more data transfer buses operable to provide non-networked data connection means that may allow the device 102 to transfer and receive data to and/or from external connected devices (e.g., universal serial bus (USB) hard drives, monitors, etc.).

In some embodiments, various disposables may be used with the device 102, such as a disposable which integrates a patient interface with an acoustic carrier (e.g., the gel and adhesive). According to some embodiments, the device may communicate data to a secondary processing system via a communications network—the secondary processing system may process received data according to data-analytics models and/or may integrate received data with previously stored data.

In FIG. 1, the device 102 is depicted along with a patient's blood vessels (noted as reference numerals 104 and 106, in this example, the carotid). In such an embodiment, the output of the device 102 may be indicative of reflected hypersonic waves transmitted by transponders forming part of the device 102, and reflecting off of a vessel of interest (in this example, the carotid artery). The received reflected signals, when processed, may produce an output indicative of hemodynamic properties of blood flow from the patient's heart 108, through the vessel of interest. The device 102 may output through the user interface 110, for example, as various readings that can be interpreted by a machine and/or a healthcare practitioner. The blood flow and/or vessel walls may be tracked using an ultrasound sensor, and denoted as reflected signals undergoing a Doppler shift. The measured Doppler shift may be indicative of the movement of red blood vessels in blood through an artery or vein relative to the device 102 over time. The reflected signals may, when measured, produce values distinct from all other vasculature, which may facilitate isolation of reflected signals from a vessel of interest. The measured Doppler shift over a span of time may form the velocity time integral, and may be indicative of the amount of blood passing through a cross section over the span of time.

The device 102 may be configured to perform automated functional hemodynamic assessments in a vessel (e.g., a carotid artery, brachial artery, femoral artery, etc.). For example, the device 102 may be utilized to perform auto-focusing of an ultrasonic source (e.g., an ultrasound probe) at a number of different depths and angles, and then collect data that best fits the structure of a targeted blood vessel. In some embodiments, the device 102 may include a chain of transducer pairs oriented in a saw tooth pattern such that, in concert, the transducer pairs produce ultrasonic waves at an angle of incidence between about 25 degrees to about 60 degrees in respect of a plane of fluid flow (e.g., the direction of blood flow through a blood vessel) through the at least one targeted blood vessel.

According to some embodiments, the saw tooth pattern arrangement may function to aim the ultrasonic beam so as to reliably generate an angle of incidence of about 25-60 degrees (or thereabout) with general anatomical angle (for normal body types of 45 degrees). Use of this angle may enable reliable detection of reflected ultrasonic signals from the body part of the individual containing the vessel of interest toward which the ultrasonic beam (e.g., a continuous beam or pulsed beam) is directed without the intervention of a specifically trained technician or other individual. Acceptable angles, in accordance with some embodiments, include +/−1 degrees, +/−2 degrees, +/−3 degrees, +/−4 degrees, among others.

Current methods require careful placement of ultrasonic monitors, often requiring the skill of an expert or trained individual in order to ensure effective readings. According to some embodiments, the saw tooth pattern arrangement may function to make available a plurality of redundant, but effective, placement options on the body part of the individual, thus making it less difficult to obtain an effective reading from the vessel of interest. The saw tooth pattern of the array may be oriented such that co-planar elements all have the same or about the same angle (e.g., relative to the skin) such that an unfocused curtain of ultrasound is emitted, the unfocused nature of the ultrasound allowing for a series of redundant positioning points for positioning the device 102.

The redundant positioning may allow for the device 102 to be used by a less skilled or, in some embodiments, even an unskilled user. Further, redundant positioning is helpful in emergency situations where non-ideal conditions in conjunction with a need for speed (e.g., individual is otherwise in great pain or dying), even for the skilled practitioner.

According to some embodiments, multiple transducer element pair designs, such as the saw tooth pattern, may also enable multi- or single element activation depending, for example, on the quality of the reflected signal received from the vessel of interest. For example, where a multi transducer element array containing 10 elements receives a reflected signal from a vessel of interest that is sufficient to allow effective functional hemodynamic monitoring, the remaining eight elements may be de-activated or may enter a low power mode. This may provide benefits to power consumption and efficiency of operation (e.g., computational efficiency) and vessel identification.

The device 102 may be functional to perform automated functional hemodynamic assessments of a number of types of blood vessels. Depending on a particular vessel operable with the device 102 at a certain time, different depths and angles may be selected. The selection, for example, may be automated, based on the application of various pre-programmed instruction sets. The selection of such parameters is a non-trivial technical problem in view of variations of human physiology, blood vessel types, and practitioner skill levels. Further, the device 102 may operate, in some embodiments, such that it may be operable by unskilled practitioners and/or practitioners having less training (who may need to rely on the device 102 to select parameters based on sensed data and/or input data). The data retrieved from the ultrasound unit may be utilized, for example, to calculate relative blood flow (e.g., amount of blood heart beat or unit time), and a potential advantage may enable variance in how the probe is oriented to the particular vessel being examined.

The device 102 may be configured to detect relative blood flow (in one or more directions, such as forward or backward flow) through a particular vessel (e.g., the carotid artery, brachial artery, femoral artery, jugular, etc.). The device 102 may further be configured to indicate the level of cerebral perfusion that has occurred. The device 102 may further be configured to indicate whether the return of spontaneous circulation ("ROSC") has occurred. Where functional hemodynamics are measured during CPR, the device may be adapted to measure functional hemodynamic parameters (e.g., fluid dynamics) in a "binary" mode (i.e., fluid is either flowing through a vessel, or it is not). In other embodiments, the device may be adapted to provide a relative measure of a hemodynamic parameter such as the amount of fluid flowing through a cross-section of the vessel over a particular period of time (e.g., carotid, femoral, brachial, etc. blood flow rate). Measurement of relative carotid flow rate may be the most effective way to automatically detect ROSC. In detecting and determining ROSC, some embodiments of the device are configured to apply signal processing to identify indicative waveforms (e.g., "shark-fin shaped" pulses, or other types of pulsatile-type waveforms or cardiac waveforms) which may be out of synchronicity or occur out of phase in relation to chest compressions.

In a specific example, the identification of one or more "shark-fin shaped" waveforms may, for example, be indicative of a ROSC event. A "shark-fin" shape, for example, may include pulses having one or more rounded curved sections, for example, on a leading and on a trailed edge of a pulse. In Applicant's experiments, the "shark-fin" shape was found to be particularly representative of ROSC events.

Other shapes are also possible (e.g., pulsatile-type waveforms or cardiac waveforms), and they are indicative of ROSC events when determined to be out of synchronicity or occur out of phase in relation to chest compressions. When these out of sync/out of phase shapes are identified and determined to be more prevalent than potential noise artifacts, the device 102 can be configured to alert the rescuer to immediately stop compressions (potentially limiting damage in emergency situations).

As described in further embodiments, there may be various methods and/or techniques to aid in affixing and immobilizing the ultrasound unit (e.g., an ultrasound probe) to the local site on the patient in order to improve accuracy/fidelity of repeat measurements and, in some embodiments, provide real-time monitoring. For example, adhesives, tensioning bands, collars, pillows, etc. may be utilized. In some embodiments, housing is provided to which vascular probes could be attached and fixed to the neck at varying angles.

In some embodiments, the device 102 may be configured to communicate through one or more communication links (e.g., wired, wireless, cellular, local area networks, wide area networks, infrared, Bluetooth™) with one or more receiver computing devices (e.g., for further analysis) and/or downstream computing devices (e.g., a data centre associated with a healthcare facility). Accordingly, the device 102 may or may not have a display 110.

For example, the device 102 may be configured to provide outputs that may inform the function of other devices. The output of the measure can inform various individuals and/or machines of various hemodynamic parameters (e.g., features of the flow of blood through a vessel). For example, machines delivering cardio pulmonary respiration (CPR) can provide feedback on the efficacy and timing of chest compressions. The reader will understand that many other applications may be contemplated. For example, the device 102 may be configured to benchmark the velocity of early chest compressions (when the rescuer is fresh) based on first 3-10 chest compressions, then interpret the velocity of the blood on each compression with and providing an output (e.g., an alert, a signal, a visual indication) that informs the rescuer on how close to achieving the same efficacy in each subsequent chest compression. The feedback to the rescuer is particularly useful where the rescuer is not particularly experienced or skilled, and the feedback may be modified to indicate, for example, relative instruction sounds (e.g., a voice indicating "last compression was less effective than prior compressions), or other types of visual indications.

The device 102 may have various components to detect (e.g., monitor, track, probe, sense, determine, identify, investigate) various physical characteristics of the patient.

The device 102 of FIG. 1 may be used in conjunction with specific workflows that may be adapted such that the device 102 and the workflows intemperate to provide accurate and repeatable localization (e.g., using the ultrasound readings).

The portable ultrasound unit may, for example, be a continuous wave Doppler ultrasound module that is capable of emitting ultrasonic waves in a continuous beam, and that is accurate and fast enough to provide a real or near-real-time analysis of parameters of the fluid flow in the blood vessel, in some embodiments, free of a bulky cart or cord. The device 102 may, for example, be portable enough to be carried around by a physician (e.g., for extended periods of time) or stored for sharing by multiple practitioners (e.g., in a 'grab-and-go' charging station for physicians).

In other embodiments, a pulsed wave Doppler ultrasound may be provided instead.

Continuous wave Doppler ultrasound modules may function to measure fluid velocities along the entirety of a scanned channel. For example, where the scanned area is a blood vessel, a continuous wave Doppler method may measure the velocities of fluids traveling through the entire scanned portion of the blood vessel over a period of time. In contrast, pulsed wave Doppler ultrasound modules may only allow measurement of fluid velocities at a single point, or a very finite sequence of points, along a scanned channel.

Pulsed wave Doppler ultrasound modules may function by emitting a pulsed signal toward an area of focus for a finite period of time, then ceasing the emission of said signal and monitoring received signals in order to record a reflected frequency shift related to the original emitted signal for a finite period of time. This process is then repeated. Once the reflected signal is received, a processor calculates the velocity and flow of liquid through a channel at the area of focus (e.g., a blood vessel). Since pulsed wave Doppler ultrasound techniques require a finite signal emission period and a second finite signal monitoring period, there is a limit to how fast said techniques can accurately measure the flow of liquid through a channel—where the velocity of the fluid surpasses a certain point, temporal aliasing (a phenomenon whereby a recorded signal appears distorted due to a recording system with an insufficient sampling rate). This mode of operation can be described as "half-duplex".

Continuous wave Doppler ultrasound modules function by emitting ultrasound signals in a continuous beam along a channel and continuously monitoring the multitude of reflected frequency shifts via a detector. This mode of operation can be described as "full-duplex" as the continuous wave Doppler ultrasound is continuously emitting and receiving signals. A potential advantage realized by this mode is that it enables the measurement of high-velocity flows of liquids through channels (e.g., blood through blood vessels) that could not be accurately measured using pulse wave Doppler ultrasound techniques due to the above-described temporal aliasing problem.

The device 102 may further include and/or be associated with a locating disposable that may be affixed once to the patient for various measurements, the measurements of which can be compared with one another. The device 102 and/or the locating disposable may require a level of ease of use and sufficient accuracy such that practitioners and care centres may readily adopt its usage.

The device 102 may be battery powered and may use a transducer array which may function to measure the Doppler shift produced by fluid passing through a vessel (e.g., a Doppler shift produced by red blood cells in blood travelling through an artery relative to the position of the device 102. A technical challenge arises in relation to ensuring that the device 102 is configurable to identify (e.g., delineate, distinguish) flow through particular vessels (e.g., distinguish carotid flow from the jugular vein or other confounding objects).

In operation, a patch-like (or collar-style) probe may be adhered to local area of skin on a patient under which the patient's carotid artery (or other vasculature) passes. The probe may utilize ultrasound signal processing methods (e.g., Doppler signal processing functions) to identify pulsatile flow. When the ultrasound (e.g., continuous wave Doppler) function of the ultrasound signal is directed at an opposing angle to the blood flow, a velocity-time trace may be obtained. By defining one cardiac cycle (pulse/heart beat), a unit time may be defined.

Calculating the area under the velocity-time curve (i.e., the calculus integral), the device 102 and/or a downstream device may utilize the data to determine the velocity-time integral ("VTI"), and the VTI may be multiplied by the cross-sectional surface area of the vessel over the time of one cardiac cycle (heart beat). The velocity time integral is proportional to the volume of blood that flows through a vessel per unit time. Therefore, it is a surrogate for cardiac output which is an important hemodynamic perimeter (e.g., a proxy that can be obtained based on measured physiological indicators).

The VTI can be used, for example, to track an average of VTI over a period of time prior to performing an intervention (30 s window), perform an intervention (30 s window), and to calculate average VTI over a period of time after performing an intervention (30 s window). In this example scenario, the VTI is used as a proxy to determine the efficacy of the intervention, which is useful feedback in emergency situations. For example, a portable blood flow monitoring device 102, on detecting effective treatment, may indicate via tactile (e.g., vibration motor), auditory (e.g., speaker) or visual (e.g., GUI) mechanisms that CPR should stop, potentially preventing additional trauma to the patient that otherwise would have occurred if CPR continued (e.g., broken ribs, sternum fractures, internal organ damage).

Accordingly, an automated physical measurement of a blood flow through the vessel per heartbeat may be obtained using an ultrasonic approach.

In some embodiments, an auto focusing mechanism is provided, where the device 102 may conduct a validation protocol to identify which settings are optimal (e.g., frequency, angle) for the patients body, patch placement, and/or other parameters. A challenge with conventional technologies is that the selection of these signals is non-trivial and may often lead to a high level of training required. For example, this aspect of the technology aids in allowing un-trained or less trained personnel to use the device 102 reliably.

A computing device may apply an algorithm in conjunction with detected readings to determine the patient's velocity time integral (VTI, pre-challenge); prompt the physician for a fluid challenge (e.g., passive leg raise); detect and/or calculate a post-challenge VTI; and deliver an assessment of the patient's fluid responsiveness (increase of >10% VTI or output following fluid challenge). A ratio may be found between pre and post-challenge VTIs, and other thresholds may be used for assessments (e.g., 10%, 5%, 3%, etc. and may be indicative of an increase or decrease). Where a condition is broken (e.g., as provided through a business rule), or a trigger triggered, a notification may be generated and/or provided (e.g., an alert, a sound, a display, a pop-up).

A display may, for example, aid the physician by providing various types of views, some views having various transformations (e.g., a simplified view), annotations (e.g., display markers, dynamic markers), analytics (e.g., determined aspects, averages, means, medians, identified aberrations), and/or a raw data view. For example, a post-/pre-VTI ratio may be determined, and a 10% or greater ratio may be indicative of a fluid responsiveness condition. Accordingly, some embodiments may be utilized to detect and/or determine various characteristics in relation to a carotid anomaly, or detect a carotid anomaly or an anomaly regarding another vessel of interest (e.g., brachial artery, femoral artery, etc.).

There may be other types of ultrasound devices that can perform flow monitoring, however, drawbacks with conventional devices may be those typical of a multipurpose device: they are large, difficult to use, and may often require lengthy training or experience.

Figure 2:
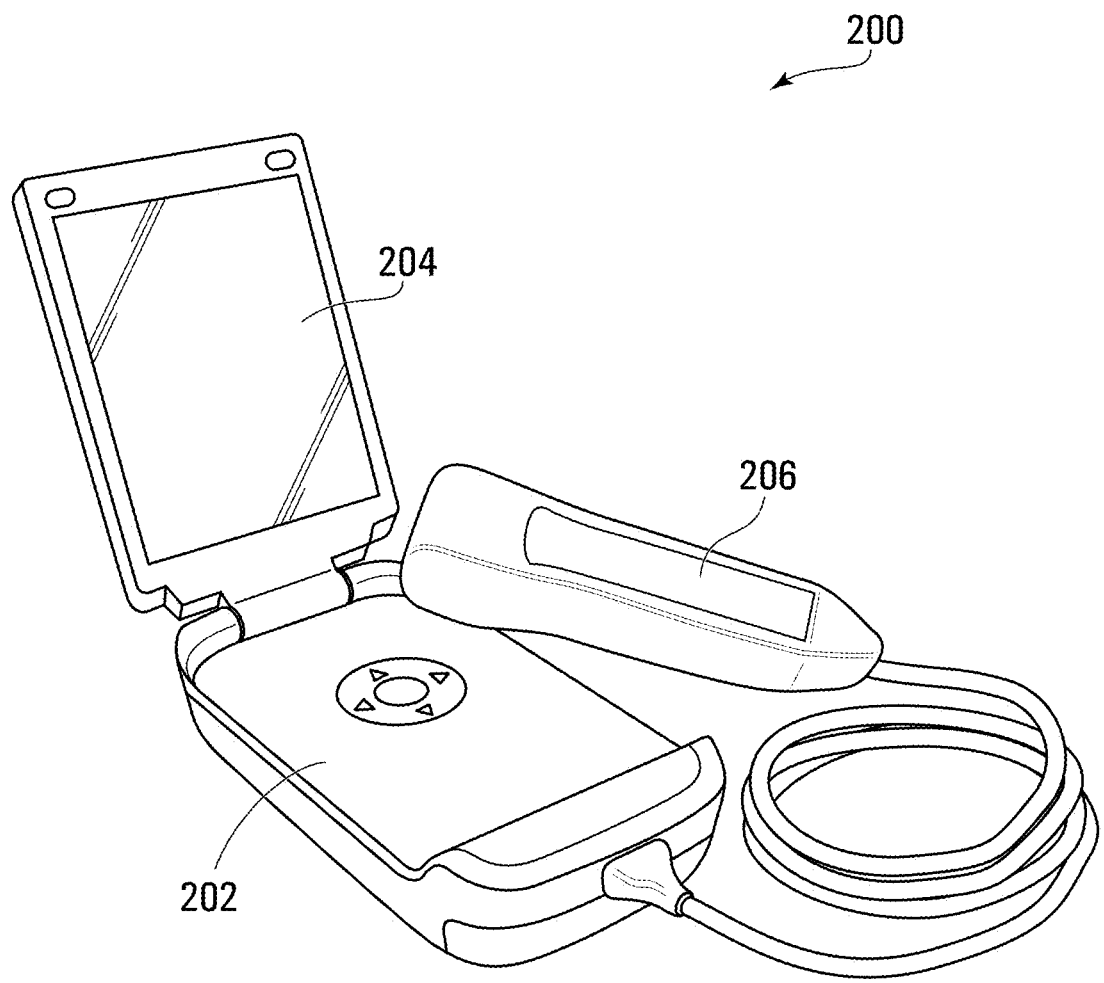
FIG. 2 is illustrative of a conventional ultrasound unit, the GE VScan™ having a display, and a probe.

The device 102 of some embodiments may be configured such that there may only be a minimum level of required hardware to effectively monitor blood flow, and may reflect a trade of multi-functionality for size, providing additional benefits as in relation to operation for use with carotid flow procedures. At FIG. 2, a conventional ultrasound unit, the GE VScan™ 202 is pictured, having a display 204, and a probe 206.

Other catheter-based technologies may also be used for hemodynamic monitoring, but the conventional products may be cumbersome and add risk in the context of various procedures. Pulmonary artery catheterization is another technique that may be available for hemodynamic monitoring, wherein a catheter is inserted into the pulmonary artery via the vena cava to directly measure cardiac output. Pulmonary artery catheterization can measure right atrium, right ventricle, and pulmonary artery pressure, as well as left atrium input pressure, but a major drawback is that the catheterization is invasive and limited to surgical use. Pulse Pressure Waveform Analysis (PPWA) is another technique that utilizes the arterial waveform, obtained either from an arterial catheter or a finger probe, in order to calculate the stroke volume (SV) and the systemic vascular resistance (SVR), but complications may arise in view of non-linear and varying arterial wall compliance.

Phase shift technology/bio reactance approaches may be considered for use, wherein when an AC current is applied to the thorax, the pulsatile blood flow taking place in the large thoracic arteries causes the amplitude of the applied thoracic voltage to change. Research, however, has indicated poor performance in relation to critically-ill/post-operative patients; further, this approach may be hindered by environmental factors, such as overweight or patients which perspire heavily. Gas rebreathing techniques may also be used in relation to estimating CO non-invasively, but while easy to use, they have been shown to be adverse affected by spontaneously breathing patients. Septic Shock Algorithms may use aggregated historical data to predict the onset of septic shock, which can be diagnosed through blood pressure readings.

In some embodiments, the device may produce outputs functioning to allow detection of various types of compensated shock. Compensated shock may be defined, in an adult example, as systolic blood pressure above 90 mm Hg while exhibiting signs of inadequate perfusion (e.g., tachycardia). In such situations, the device may transmit an alert signal via a sensory output device.

In an example method, compensated shock can be determined as a ratio between HR/systolic blood pressure. However, this is not a very sensitive method as blood pressure takes a long time to change during shock.

An improved method of some embodiments determines/generates a prediction of compensated shock by generating a comparison between heart rate and the measured velocity time integral (e.g., a HR/VTI ratio). The improved method generates a more sensitive marker as VTI corresponds more directly to the state of the heart. Accordingly, the improved approach enables earlier detection of patients in compensated shock. For example, in some embodiments, the device is configured to determine/flag changes in the HR/VTI ratio, and as the ratio becomes larger, the patient is flagged as potentially entering into shock (and corresponding workflows may be invoked, for example, to generate one or more alarm notifications).

Figure 3:
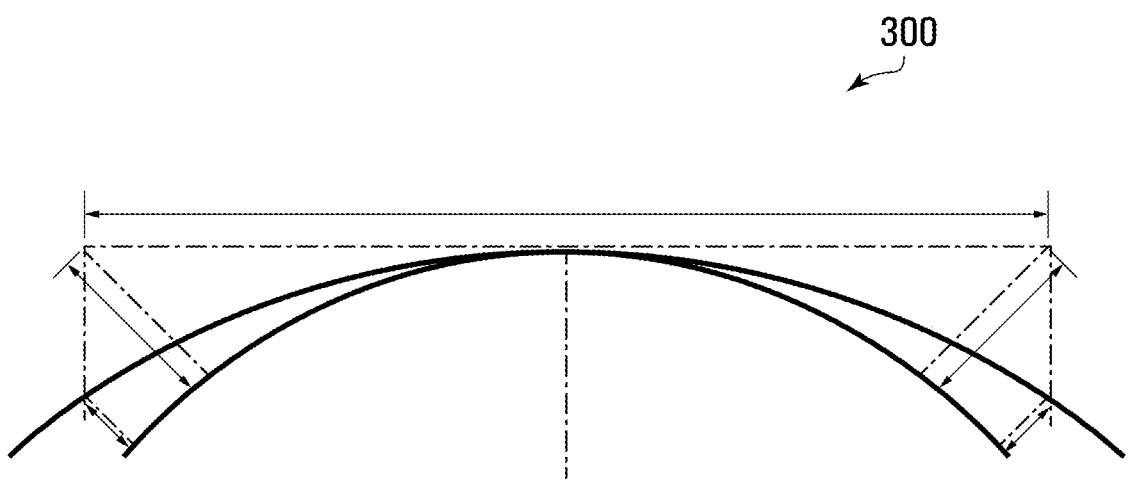
FIG. 3 is an illustration of an example neck profile, according to some embodiments.

FIG. 3 is an illustration of an example neck profile, according to some embodiments.

Patients may have differing anthropometric parameters, including, for example, carotid anthropometries, neck anthropometries, etc. These parameters may be taken into consideration, for example, as the device may need to be fitted on to and/or used in close proximity to bodily features of the patients, and thus may need to be calibrated and/or accurately positioned.

For example, the minimum size (i.e. length) of the neck may determine the maximum size of a body mounted device. The neck length for the smallest 5% of the population is roughly 8 cm, and accordingly, the maximum comfortable height of the device may approximately be 8 cm.

Neck circumference also varies from person to person. The smallest neck circumferences may be about 312 mm, and the largest about 463 mm. For a round or square device (e.g. 8 cm in diameter or 8×8 cm square), the patient's neck would have to conform roughly 14 mm at the edges, too much for patient comfort. If the device were curved, the neck would have to only conform roughly 5 mm, but a curved feature may add complexity (and likely size) to the device and/or components thereof.

As indicated in FIG. 3, the neck anatomy may be fairly consistent from patient to patient. For example, the internal diameter of the Common Carotid Artery (CCA) may be approximately 6.2 mm for women and 6.5 mm for men, ranging between 4.3 and 7.7 mm in maximum and minimum sizes (as noted in a study having a study size of 123). The standard depth for a patient's CCA may be 20-40 mm below the skin. The wall thickness may be roughly 0.75 mm. Additionally, the diameter of the CCA may expand roughly 0.5 mm with every heartbeat.

Another study suggests that the ratio of the internal carotid and external carotid artery diameters can be predicted as approximately 0.65 and 0.58 respectively (e.g., each is roughly ½ to ⅔ of the diameter of the CCA). The vertebral artery may be hidden in bone, very far away and very small. The jugular vein has blood flowing in the opposite direction (therefore "up" may have to be established).

Directional information can aid in the assessment of position. Dimensional measurements can also be used to aid in position by assuming any measurement of a 5 diameter less than 4.3 mm is likely not the CCA.

Furthermore, a relationship can be established between distance and diameter of the CCA. A CCA further from the skin implies a larger bodied patient, who would be expected to have a larger CCA.

One study placed the ideal measurement location at 15-20 cm below the bifurcation. The subclavian artery sits very close to the clavicle, and the CCA bifurcation is near the larynx (Adam's apple) meaning a reasonable measurement location is anywhere from 5-20 cm above the clavicle, or midway between the larynx and the clavicle.

Patients with larger neck diameters are likely to have a thicker layer of cutaneous tissue between the probe and the CCA. No papers studied described a correlation between bariatric patients and difficulty in reading CCA flow, meaning this may not be an issue. It may also mean that the full sized ultrasound machines currently in use are variable enough to account for these differences. This patient profile may not be suitable for the AFRU. In some embodiments, multiple transducer pairs may be arranged end to end to form the transducer array. This may enable the device to contour to different patient morphologies on the neck, arm, torso and/or thigh, etc.

Figure 4:
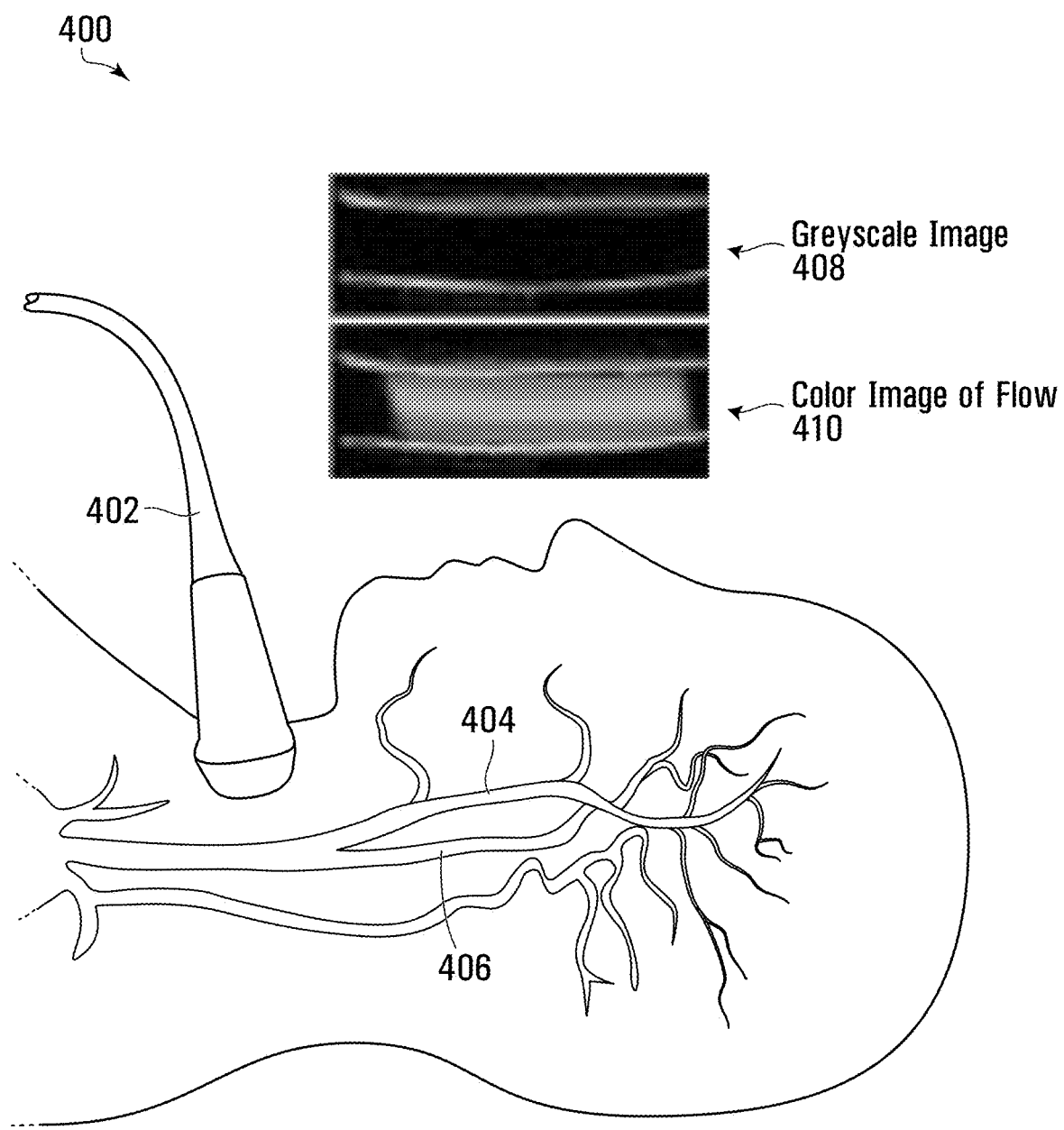
FIG. 4 is a depiction of a common carotid artery (CCA) Flow Measurement Angle, according to some embodiments.

FIG. 4 is a depiction of a CCA flow measurement angle, according to some embodiments. A probe 402 is shown for measuring flow in relation to vessels 404, being incident flow at plane 406. Accordingly, sample images 408 (greyscale) and 410 (color) are shown.

Applicants considered various approaches to the ultrasound unit and made various decisions related to the design. In some embodiments, the ultrasound unit may include a transverse and oblique array.

Other possible approaches included a single transducer or multidimensional transducers (i.e., a 2D array or a scanning 1D array). Though these other approaches still have a possibility of success, the transverse oblique array may be preferable in some embodiments. The array may be oriented obliquely (as shown by the line indicative of plane 406) to pass through the CCA such that the array can read anatomical information in the transverse plane, and Doppler signal processing information in the longitudinal plane.

In this architecture, there is a risk that suitably effective Doppler signal processing measurements may be difficult to obtain with a transversely oriented array. There is also risk that many elements will be required, resulting in a higher cost and size of the device.

As the ultrasound architecture may be an important aspect of the device, an ultrasound investigation was conducted to test the effectiveness of the transverse array configuration.

Figure 5:
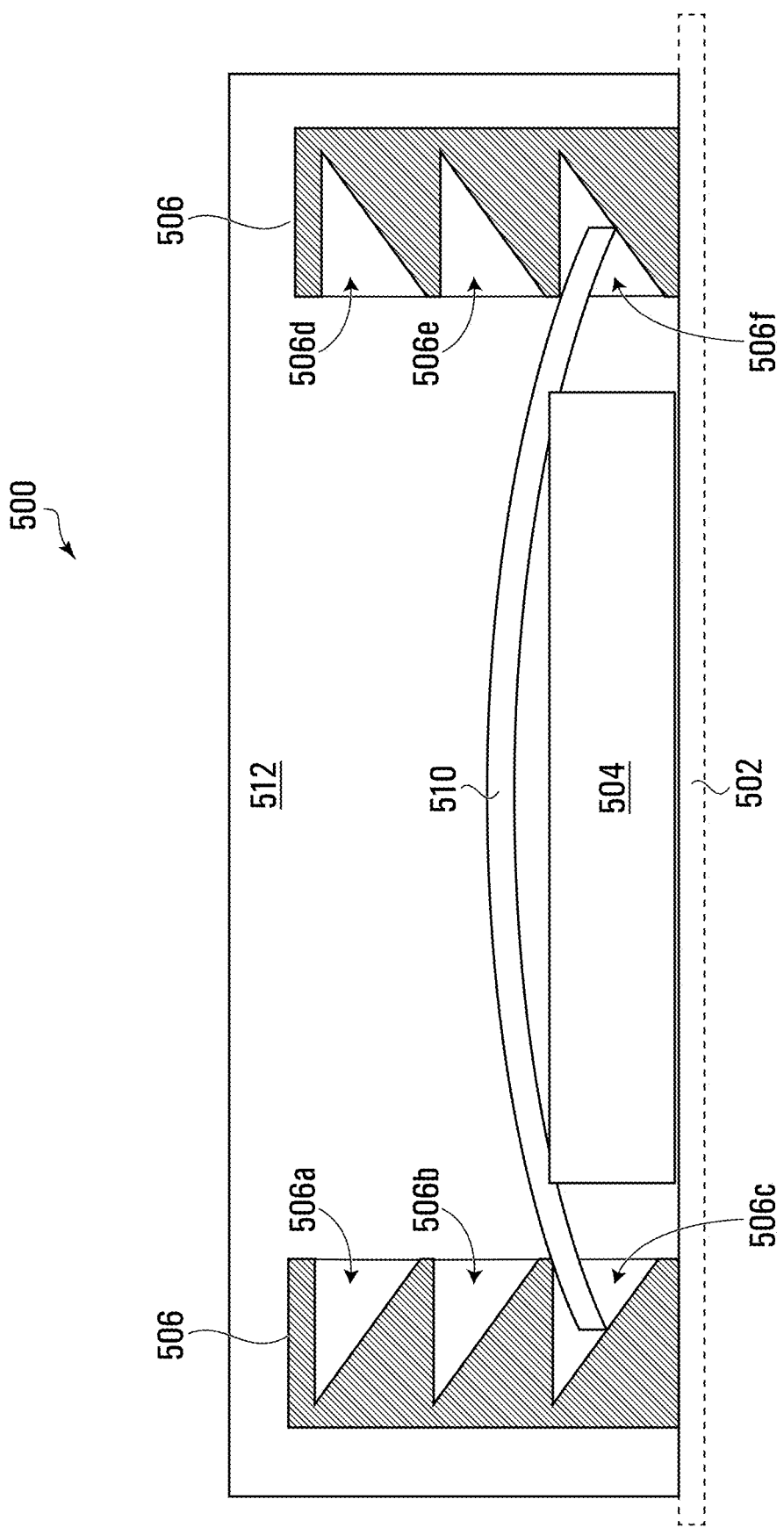
FIG. 5 is an illustration of an example tensioning mechanism for maintaining acoustic coupling between the device and a body part according to some embodiments.

FIG. 5 is an illustration of an example tensioning mechanism for maintaining acoustic coupling between a device 504 and a body part 502 according to some embodiments. The device 504 housed in a housing 512 which may adhere to the surface of a body part 502 containing a vessel of interest. The housing may further contain a tensioning cover 510 which may be coupled on one side to the device 504. The housing may further contain two or more latching mechanisms 506 which may be situated perpendicularly to the body part 502 of the individual and within the housing 512. The latching mechanisms may each contain a plurality of latching channels 506a-f which may function to receive the edges of the tensioning cover 510 when downward force is applied thereto and hold the tensioning cover 510 in place, thereby causing the tensioning cover 510 to maintain position and, by extension, apply downward force to the device 504 such that it remains secure against the body part of the individual 502. This may cause the device 504 to be situated such that it maintains a position functional to produce a correct signal and read a correct reflected signal to and from the vessel of interest (e.g., within a correct range of distances from the vessel of interest).

Figure 6:
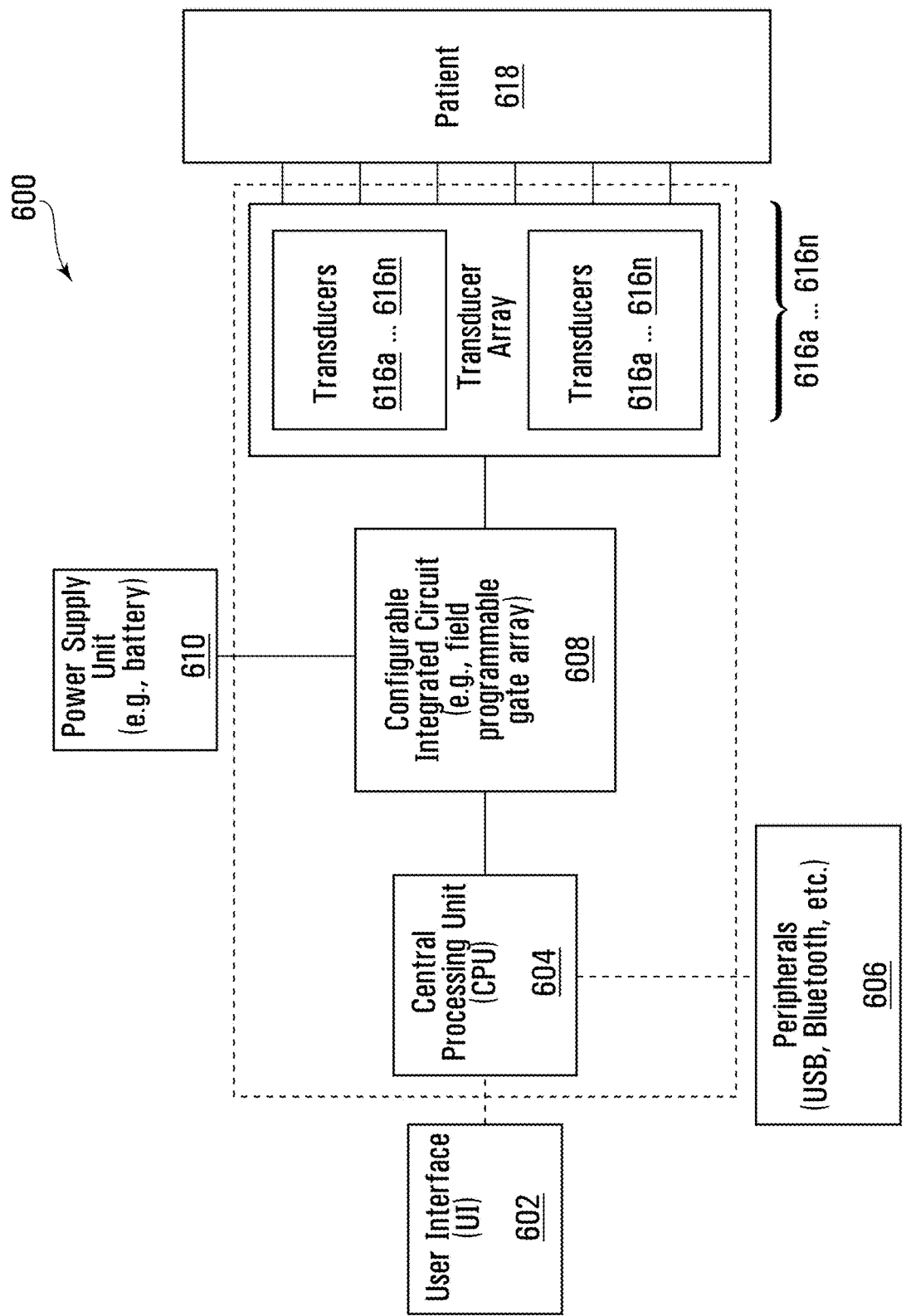
FIG. 6 is an example block schematic diagram of a device, according to some embodiments.

FIG. 6 is an example block schematic diagram of a device, according to some embodiments. FIG. 6 illustrates an electrical architecture and may include various elements of electronic circuitry, etc. The device may be implemented in various forms, including, for example, by software, hardware, embedded firmware, and/or a combination thereof.

A user interface 602 may be provided for various input I sensory-output functionality, including the ability to receive parameters, etc, from users (e.g., patients, clinicians). Output functionality may be used to, for example, provide a graphical interface for clinicians and/or to communicate information to downstream computing systems (e.g., a clinical data center).

There may be various data storage units included for storing data (e.g., raw data, pre-processed data, processed data, post-processed data), and there may be one or more processors 604 utilized for conducting various determinations and/or calculations. The device may also, in some embodiments, have on-board memory that may be used to support various functionality, such as processing data for display to a clinician, etc. Various peripherals 606 may be utilized to provide various input signals and/or to receive various outputs (e.g., through USB, Bluetooth, etc.). The processor 604, for example, may be configured to control the peripherals 606, and the user interface 602. Ultrasound components may be provided, for example, through an ultrasound front end 612, a probe, transducers 616*a* . . . 616*n*, which may be placed on and/or in proximity to a patient 618. A power supply 610, (e.g., a battery), may be utilized to supply power to the ultrasound components.

In some embodiments, the user interface 602 may be provided on a separate computing device, communicating with the Central Processing Unit ("CPU") 604 via one or more Peripherals 605, hence the user interface 602 is depicted as connecting to the CPU 604 via a dashed line.

In operation, the front end may be provided and, in some embodiments, may include an eight-channel integrated circuit that may include the ultrasound front-end 612, the probe 614, and the transducers 616*a* . . . 616*n*. Signals passing through the front-end first may be amplified and/or filtered, and then passed through an anti-aliasing filter which may remove frequencies that may be too high to be sampled. These signals may then pass through an analog-to-digital converter and may be provided to a configurable integrated circuit (e.g., a field programmable gate array (FPGA), or a custom integrated circuit) 608 as, in some embodiments, low-voltage differential signals (LVDS).

An ultrasound emitter may be utilized to produce the high-voltage signal needed to drive the ultrasound transducers. The emitter may be provided a +60V and a −60V power supply, and controlled by low-voltage logic signals from the configurable integrated circuit. Other voltages and/or power supplies may be utilized and the above is provided as an example.

The configurable integrated circuit 608 may be configured to control the emitter and receive LVDS signals from the front-end. The configurable integrated circuit 608 may be configured to perform digital signal processing that may be utilized to both send and receive signals, including beam-forming and Doppler shift computations.

The CPU 604 may host the operating system of the device, and may liaise between the configurable integrated circuit 608, user interface (UI) 602 and any peripherals 606 that may be added to the system and/or perform post-processing on signals received from the configurable integrated circuit 608.

The UI 602 may include an LCD touchscreen and/or an LCD screen with buttons. Other types of displays may be contemplated. Indicator lights, comprising for example LEDs, and indicators sounds generated from a speaker may also be part of the user interface 602 to provide feedback to the operator. In some embodiments, feedback corresponds to operating conditions of device 102 in order to direct the operator to orient device 102 to a desirable and/or acceptable local site on the patient. The purpose of this direction may be to permit full operability of the device with a minimum of training or experience. If the device is required to be connected to the cloud, an onboard Wi-Fi module can be included along with additional peripherals 606 such as Bluetooth or USB.

A printed circuit board (PCB) may be provided to host some or all of the electronic components within a structure (e.g., a housing, a base). In some embodiments, the device may be powered by a rechargeable or replaceable battery, which may be used to drive both the ultrasound and/or the other electronics (e.g., LCD screens, etc.).

As size is a consideration, lithium-ion technology may, in some embodiments, be selected as an option for compact power density. Operating under the assumption that these batteries typically can store 77,000 Ah/cm$^3$ (amp-hours per cubic centimetre), the battery in the device may have to be, for example, 125 cm$^3$ for 1 hour of continuous active use. A Li-ion battery of this size may typically weighs about 250 g. Additional lifetime can be achieved by adding a larger (and heavier) battery, which may be suitable for a larger embodiment.

Figure 7A:
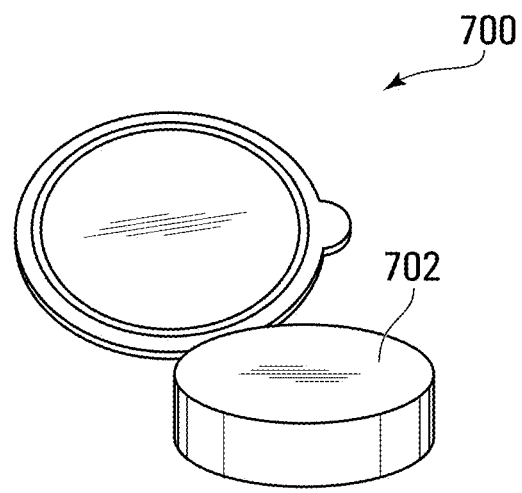
FIG. 7A-7B is illustrative of some example components that may be utilized for interfacing with a patient's body, according to some embodiments.
Figure 7B:
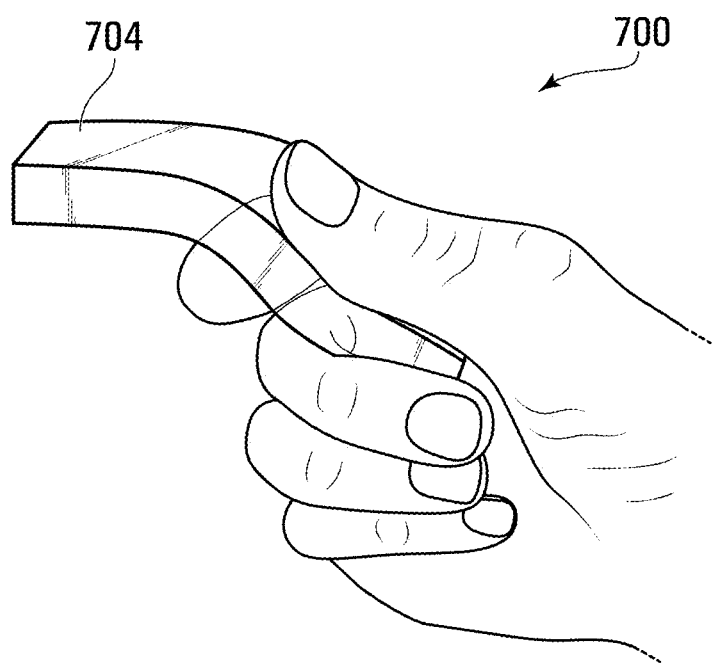

FIG. 7 is illustrative of some example components that may be utilized for interfacing with a patients body, according to some embodiments. The method with which the device interfaces with the body may be an important factor for consideration. Such a component, for example, may be a "disposable" to connect (acoustically) the probe to the skin, and connect (mechanically) the device to the patient. Sample disposables are indicated at 702 and 704.

In some embodiments, the disposable may integrate these aspects for quick application and disposition. This may avoid the disadvantage of applying ultrasound gel separately, which creates variability and mess.

In some embodiments, an approach includes combining the requirements into one solution: applying an acoustically transmissive adhesive (i.e., the adhesive also serves as the gel).

In some embodiments, the requirements may be separated: a material is provided for acoustic coupling and a material is provided for physical connection.

An example design may include utilizing an adhesive ring with a gel pad center. The adhesive connects the device and the gel (solid or liquid) provides an acoustic connection. The user would simply peel back the inside of the disposable stick it to the device, and then remove the cover of the patient side immediately before application.

The disposables may not need to be sterile (unless applications to open wounds are included in the indications), but should be held to a level of cleanliness typical of the industry.

Disposable ultrasound pads such as Rich-Mar AutoGel™, BlueMTech™ and Aquaflex™ ultrasound gel pads, may be provided to replace ultrasound gel (for the purposes of limiting cleanup) and may be utilized with the device. These pads may need to be wetted with water, and a standoff pad may be used to position the probe away to get a clearer picture of superficial areas of the skin (for example, ATS™ phantoms).

In some embodiments, a custom sized block can be centered under the probe head, adhered on one side to the device and covered on the other side by a dust cover that also keeps the disposable wetted.

As an alternative, ultrasound gel may be utilized. Gel could be pre-applied in a cavity in the disposable. A similar peel-back cover could expose the gel and make it ready for application. After use, the gel may have to be wiped off the patient.

An alternative method of acoustic coupling is a liquid filled pad. Similar to an ultrasound pad in its function and composition, these bags are filled entirely with liquid. A thinner liquid eliminates the likelihood of bubbles in the medium, but adds issues at the wall interface and with filling. For these reasons, liquid pads may be a less desirable alternative to those listed above.

In some embodiments, a tensioning material (e.g., a tension bandage) may be positioned around the body in order to provide a force normal to device 102 and ensure sufficient acoustic coupling.

Figure 8:
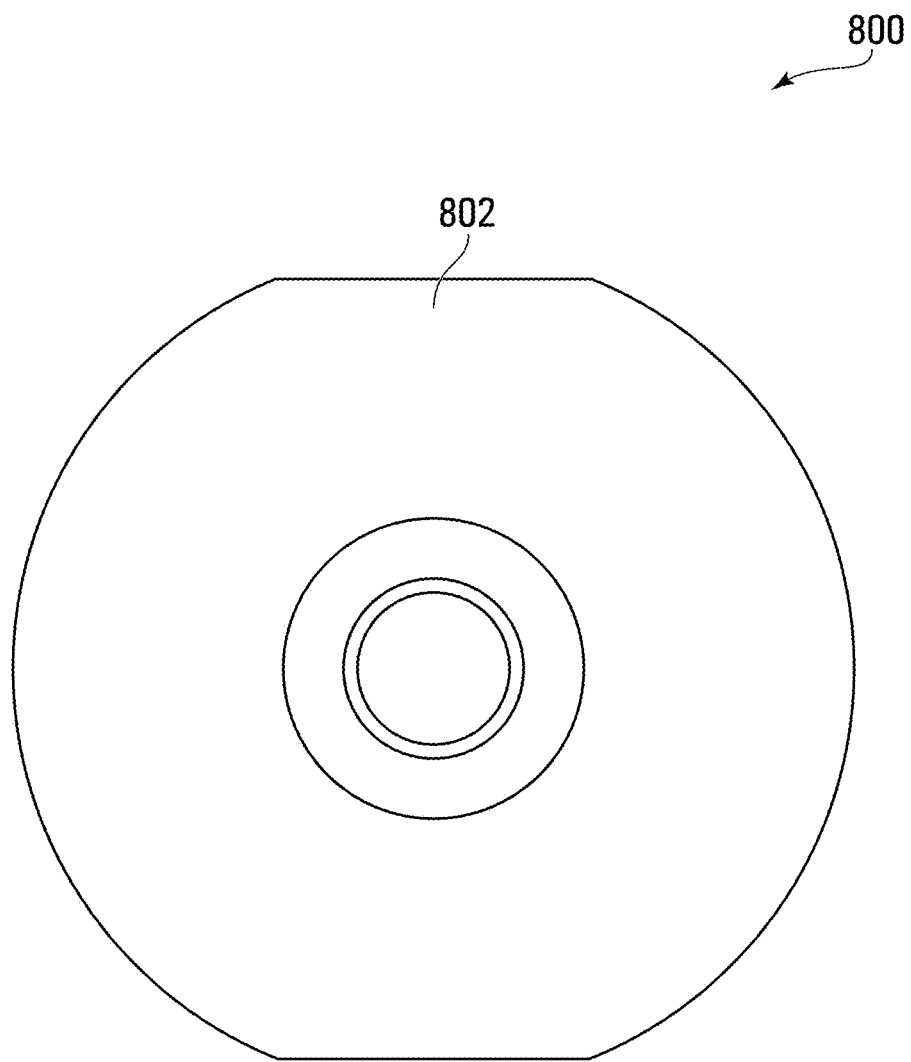
FIG. 8 depicts an example adhesive by 3M™.

In some embodiments, adhesives may also be utilized. FIG. 8 depicts an example adhesive by 3M™. Adhesives may by hypo-allergenic and may stay in place for a number of days. The adhesive 802 may help keep a device and/or a portion thereof positioned in the target local site on the patient.

Silicone may be used as a protector and an acoustic coupling material for the probe/human interface, often used in conjunction with gel. For limited movement across the patient's skin, (e.g., with some embodiments of the device), the need for gel may be reduced and silicone alone might be effective. A drawback to silicone is a reduced speed of sound, which may require an algorithm to correct.

The device may require a mechanical housing that may vary in detail between embodiments. A rigid two part housing, for example, may be sufficient to provide a structure, with standoff points to hold the electronics. The housing may include spacers between components to avoid rattle or internal movement. The housing may need to be cleanable, and so may include gaskets to prevent water ingress at the seam, display, and buttons (keypad membrane).

Heat management may be an important consideration. The device may consume significant amounts of energy during use, and accordingly, the hot features of the device may need to be kept away from the patient to reduce the risk of burning (e.g., must be less than 43° C. per ISO 60601).

If the heat generation is excessive, numerous strategies can be utilized, such as insulation or heat fins, designed inconspicuously into the exterior of the housing. A plastic housing may be a natural insulator but may cause the electronics to overheat.

A metal housing may have advantageous attributes: protecting the electronics at the expense of patient safety. If an embodiment is applied that does not connect to the patient directly then heat protection may not be a requirement.

If the housing is plastic, injection moulding can be used for manufacturing. If a metal housing is used, numerous options are available, though some may be more costly than injection moulding.

In some embodiments, the device may be provided as a single part. In some embodiments, the device is provided in having two or more parts; these parts may comprise a body, a probe, a separate computing device, a stand-alone cart, among others. For these embodiments, a probe wire may be provided to connect the body of the device to the probe.

Wires for this application may be available and may need to be strong enough to avoid pullout if the patient moves or the device falls. The probe itself (or the connecting surface on a one-part device) may benefit from a silicone interface piece, to protect the device and allow some conformity.

FIGS. 9A-9C, 10, 11A-11C, 12A, 128, 13A-13C, 14A-148, 16, 17 may be illustrative of some sample embodiments of the device.

Figure 9A:
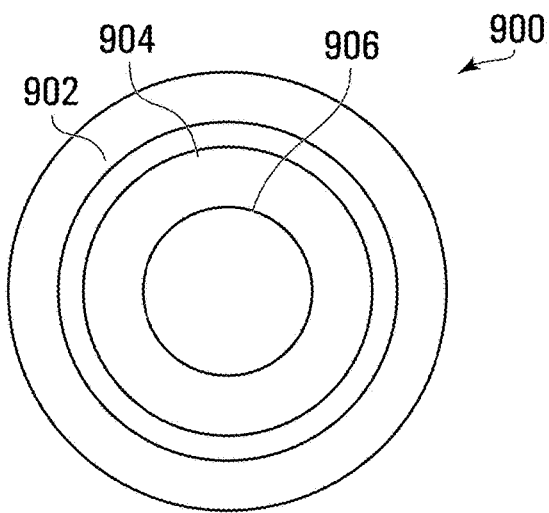
FIG. 9A-9C illustrate a pocket-size embodiment.
Figure 9B:
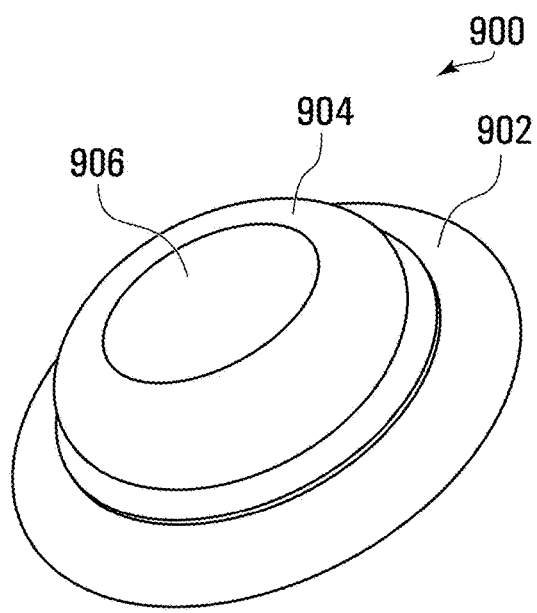
Figure 9C:
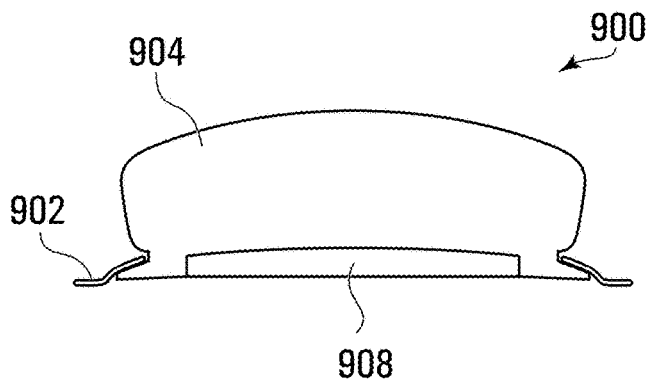

FIGS. 9A-9C illustrate a pocket-sized embodiment; FIG. 9A provides a top elevation view, FIG. 9B provides a perspective view, and FIG. 9C provides a side cross-sectional view, according to some embodiments.

As depicted in FIGS. 9A-9C, an embodiment may include a pocket sized, body mounted ultrasound device that can be carried around by a clinician (e.g., the attending physician). The device may have an adhesive ring 902, a body section 904, and/or a display 906. The adhesive ring 902 may provide an adhesive force between the periphery of the body section 904 and the local site on the patient's skin. A concave space 908 may be provided for a gel pad or liquid gel.

The size of this embodiment may be reduced by using a number of strategies, including, for example: offloading processing and display to another device such as a tablet (or smartphone), changing its geometry to rest partially elsewhere, measuring flow in a different artery (to reduce comparative size), or reducing the battery life or removing it entirely (plug-in power only).

Figure 10:
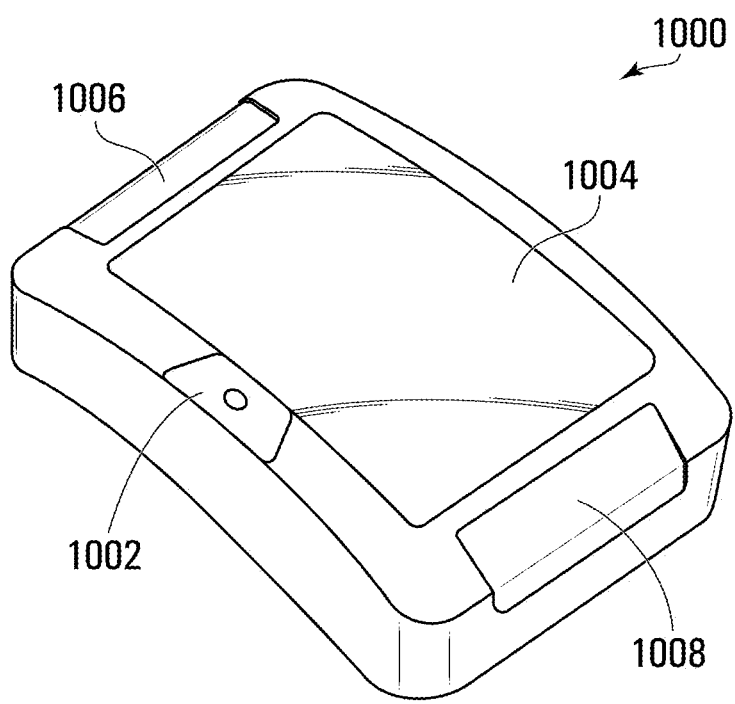
FIG. 10 is an illustration of a pocket sized embodiment.

FIG. 10 is an illustration of a pocket-sized embodiment. The embodiment may have display 1004, a power button 1002, and other buttons 1006 and 1008 that may be used, for example, to perform various input and output functions.

Figure 11A:
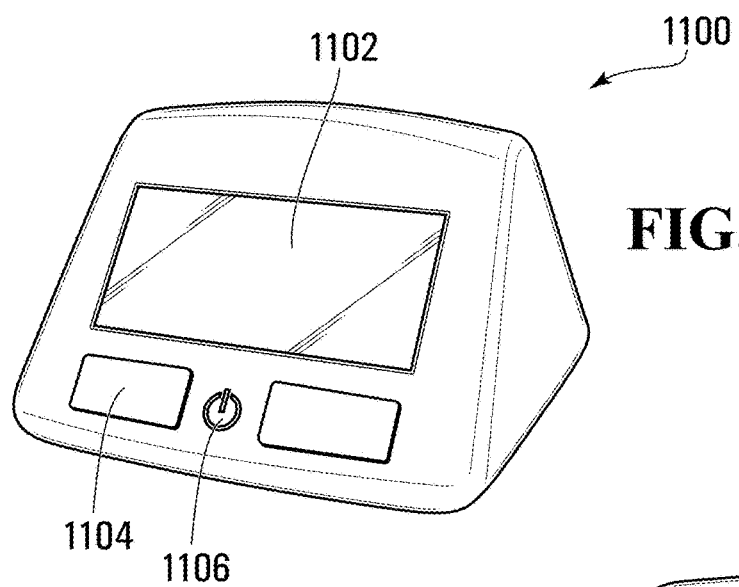
FIGS. 11A-11C are illustrative of a small embodiment with a coupled probe, according to some embodiments.
Figure 11B:
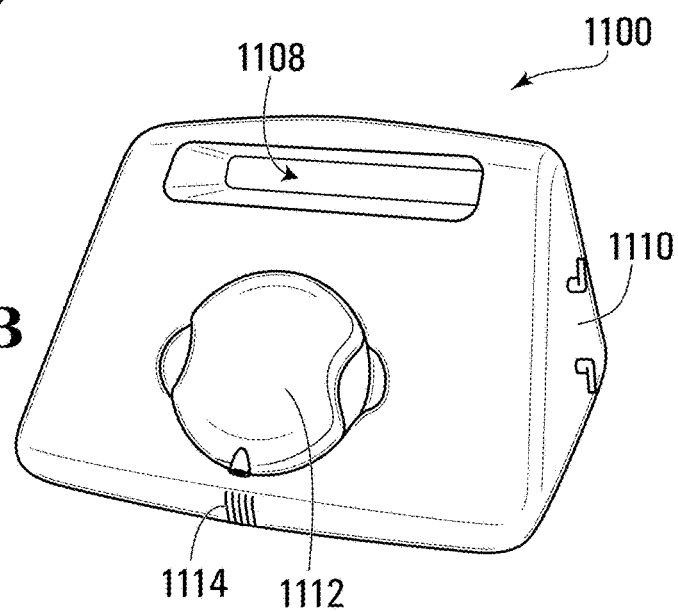
Figure 11C:
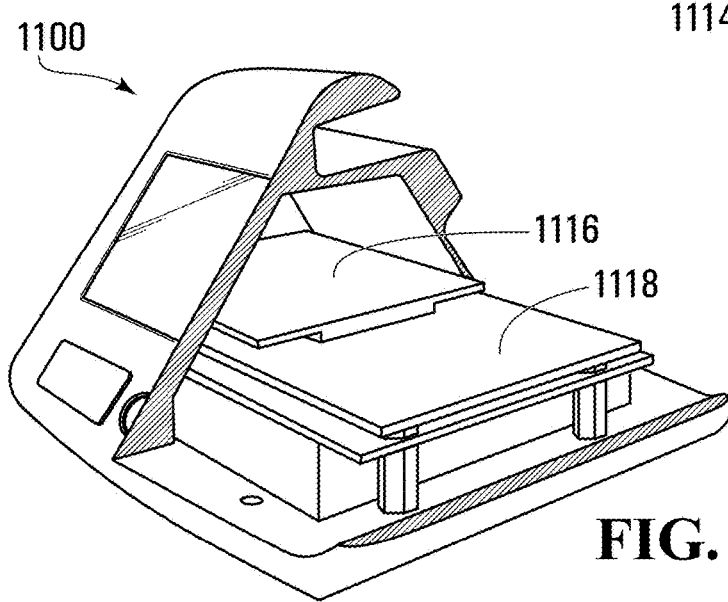

FIGS. 11A-11C may be illustrative of a small embodiment with a coupled probe, according to some embodiments.

FIG. 11A is a front perspective view of the embodiment; FIG. 11B is a rear perspective view of the embodiment; and FIG. 11C is a partial view of the embodiment. The device, may, for example, have a display 1102, control button 1104, power button 1106, an integrated handle 1108, a cable management apparatus 1110, a probe 1112, a charging port interface 1114, a printed circuit board stack 1116, and a battery 118.

The footprint and height of the device illustrated in FIG. 11A-11C in some embodiments may be approximately 6×6 inches and 4 inches respectively.

A coupled probe may provide a lower risk alternative to the pocket sized unit, while still being small and portable. The adhesive probe-patch may be coupled to the base unit via a cable.

The clinician (e.g., a physician) may place the unit on the examination table anywhere within range of the patient's neck, and extend and connect the probe. The probe may stay in place during the examination and possibly longer (for repeated exams). The device may be powered by a larger, more powerful battery than possible in a pocket-sized unit, but is also can support a wall plug for heavy use.

As the device may (in some embodiments) be too large to be carried around constantly, the device may be left at the charging station between patients, further extending battery life. The device may also be large enough to carry a gel holder, or an area to keep extra disposables. The device may include Wi-Fi and/or Bluetooth connectivity, or can transfer data via a base station. In other embodiments, the device may be miniaturized for portable use.

Figure 12A:
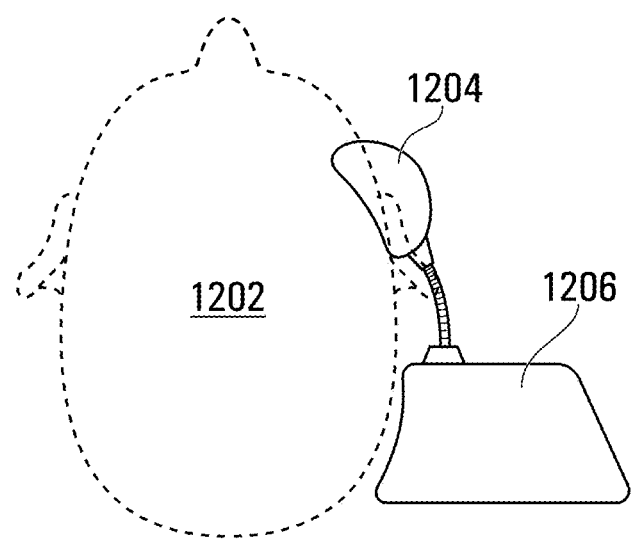
Figure 12B:
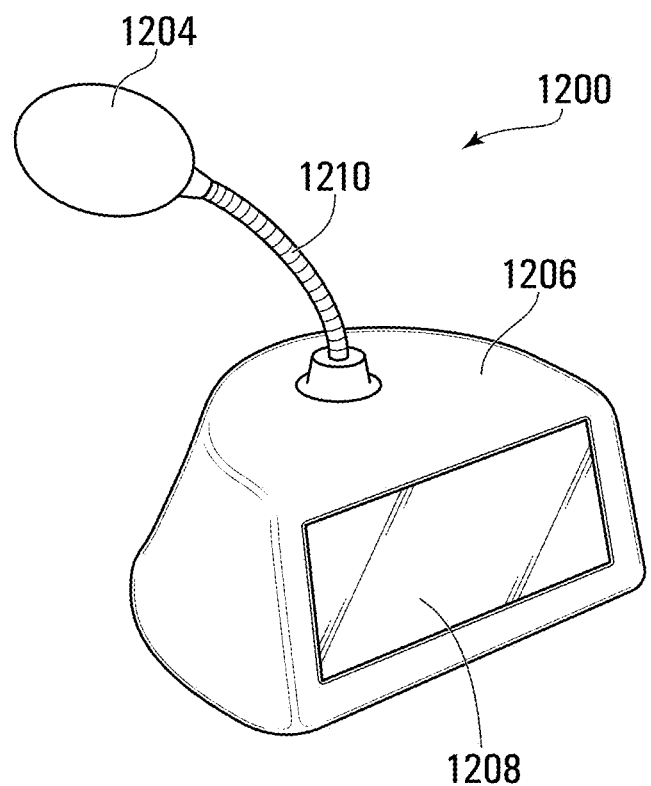

FIGS. 12A-12B and FIGS. 13A-13C may be illustrative of a small embodiment with integrated probe, according to some embodiments. FIG. 12A is a side view of this embodiment, and FIG. 12B is a perspective view of this embodiment. FIG. 13A is a perspective view of a second version of the embodiment with integrated probe being held at a handle, FIG. 13B is a perspective view of the second version; and FIG. 13C is a side view.

For example, the embodiment may include a probe 1204 for use with a patient 1202/1310, a base 1206, a display 1208/1306, and an adjustable neck 1210/1305. In some embodiments, a handle 1312 is provided. In these example embodiments, the device does not have a separated probe. Instead, and area of the main chassis contains the ultrasound head which may be placed against the patient.

Similar to the coupled probe model described above, these embodiments may contain a larger battery, a plug, wireless connectivity, and may contain storage for disposables. The embodiments may be simpler in design and use than the coupled probe, and more durable. A disposable may not be necessary, or if necessary may be a simpler disposable.

A cart embodiment is provided at FIGS. 14A and 12B; FIG. 14A is a front perspective view of a cart embodiment, and FIG. 14B is a side elevation view of the cart embodiment. The application on a medical cart may provide some advantages. For example, the central architecture does not differ significantly to other carts: the device 1402 may be provided on a cart apparatus 1406, having a handle 1404, and a base 1408. The embodiment may include a computer, monitor and screen 1410, with an ultrasound probe 1412, which may aid in simplifying the development process though the use of commercial components. Less effort may need to be focused on miniaturization and integration than a more aggressive size.

The cart embodiment may also avoid logistical issues that may be present with portable units: for example, the embodiment may be unlikely to be lost or dropped, it may not require an area on the patient's bed to be positioned upon, and can be easily plugged in (or battery powered) with room for a long cord. The device may also not require an included charging station, and may thus be marketed as an individual unit.

The device may include a chassis 1206 and a user interface 1208 (i.e., a large touchscreen), and a probe 1204 that may differ significantly from other ultrasound units.

The probe 1204 may include a small adhesive patch at the end of a connection cable 1210 which can be installed on the patient and remains stuck during the procedure (or longer). The software may be configured to automatically find the CCA and to obtain readings, displaying only the results to the clinician (e.g., a physician) and eliminating the need for ultrasound expertise.

Figure 15:
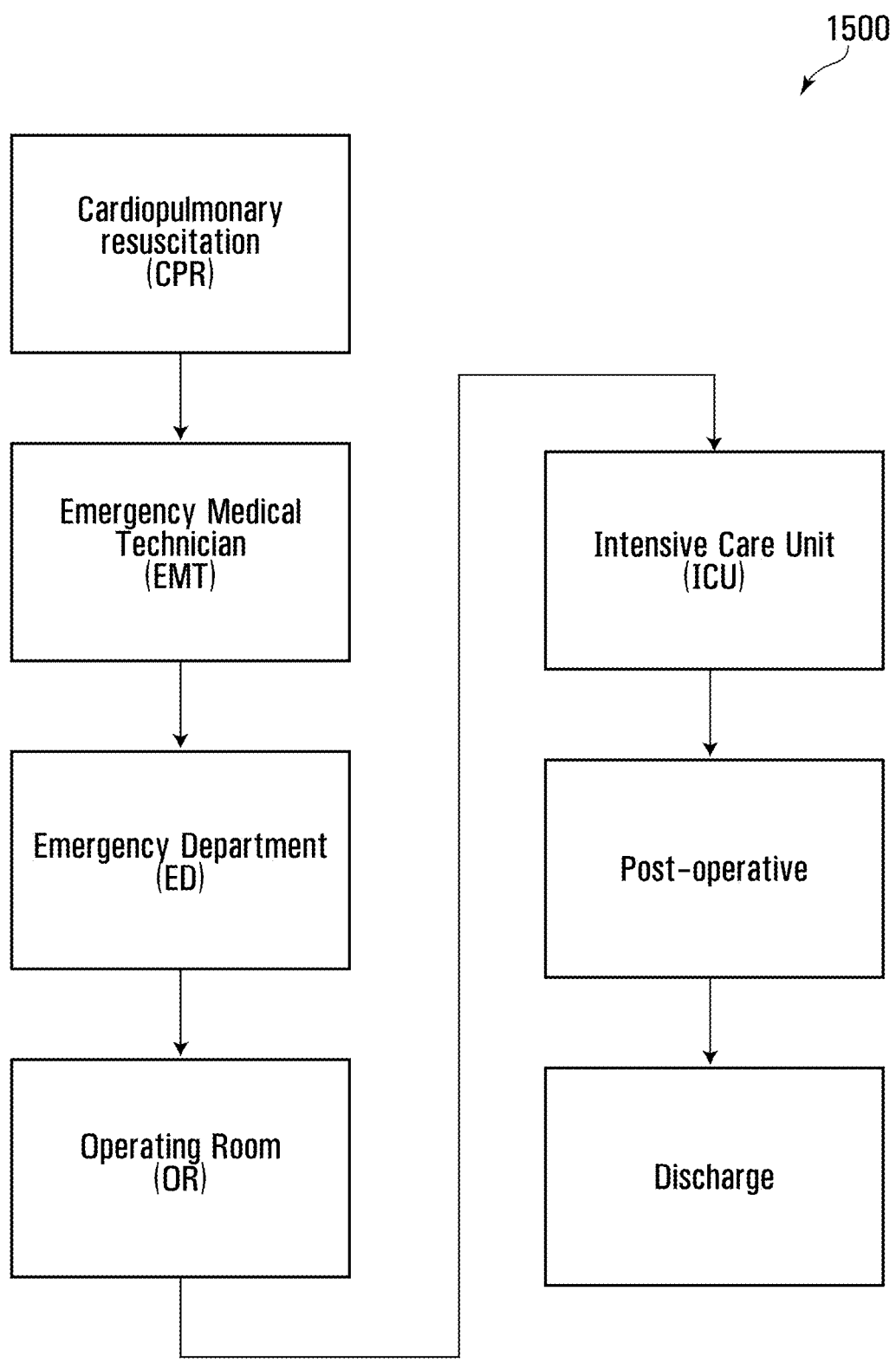
FIG. 15 is a flow diagram displaying the typical stages of medical care a patient may undergo in the event of critical illness.

Some embodiments are adapted to respond to a protracted period of patient care. An example patient-care profile 1500 is provided in FIG. 15. Assessment of functional hemodynamic parameters (e.g., fluid dynamics) may be desirable at each phase of the patient-care profile 1500. Different care-providers may be responsible at designated phases. A functional hemodynamics measurement device that is unique to a patient may be desirable in order to provide continuous monitoring between phases and care-providers. Similarly, a functional hemodynamics measurement device that is unique to a care-provider may be desirable to provide monitoring of functional hemodynamics measurement to a plurality of patients.

Figure 16:
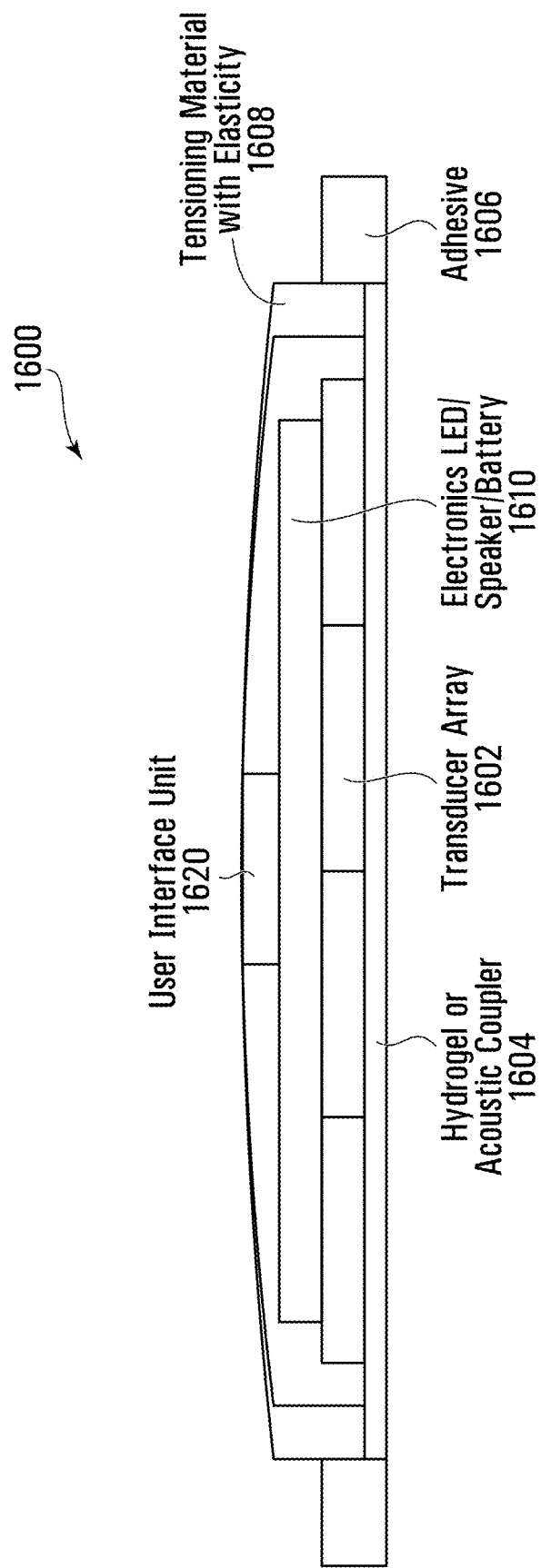
FIG. 16 is a cross-sectional diagram of a device according to some embodiments.
Figure 17:
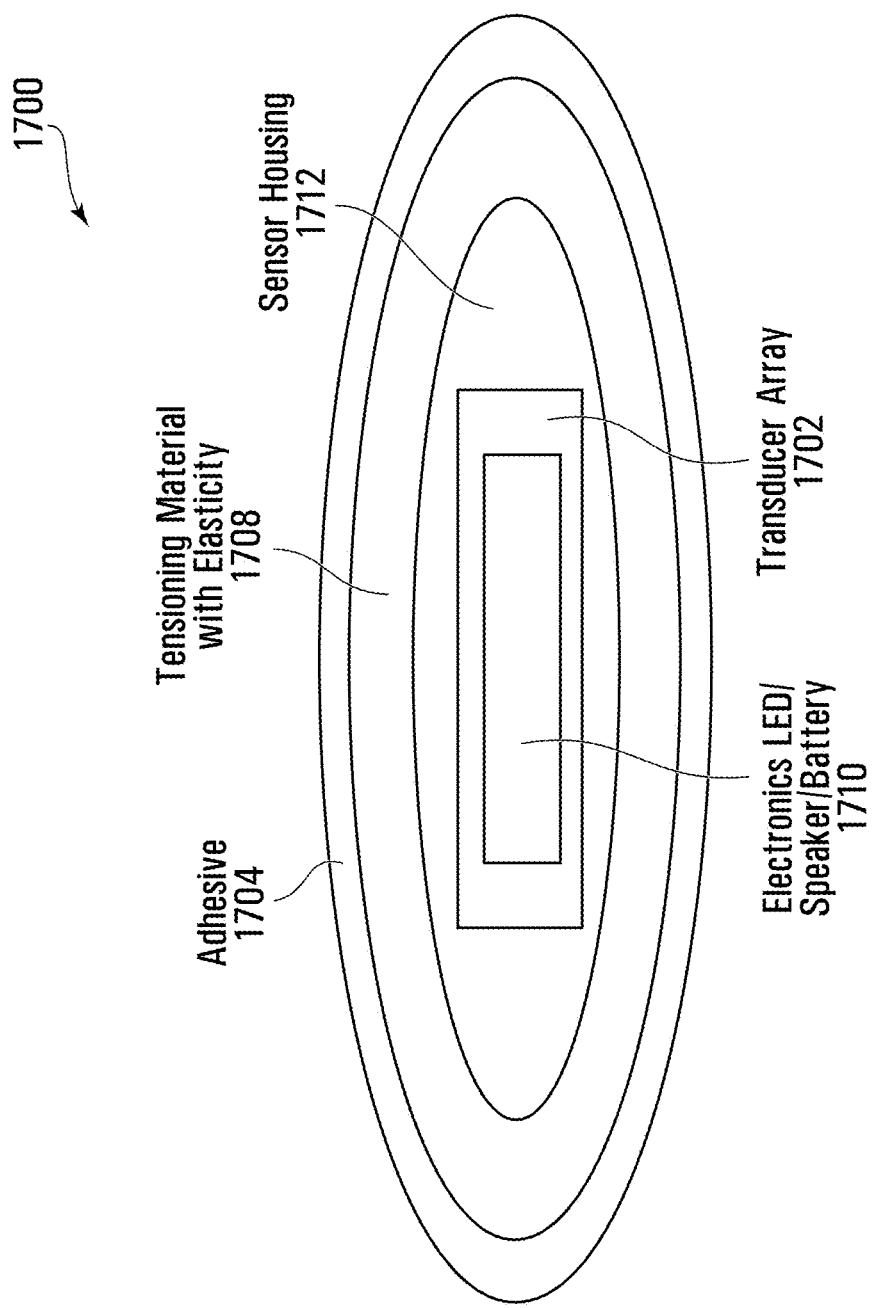
FIG. 17 is a top view diagram of a device according to some embodiments.

A cross-sectional view and overhead view of some embodiments of the device are provided in FIG. 16 and FIG. 17 respectively. In some embodiments, an adhesive 1606/1704 may be employed to fix the device to the local site on the patient's skin; a tensioning material 1608/1708 may further be employed to apply a force normal to sensor housing 1612/1712, and towards the local site in order to fix the device relative to the local site. The tensioning material 1608/1708 may comprise a band, to be slug around the patient in order that tension may be adjusted by altering the length of upstretched band. The tensioning material may further be elastic, in order to eliminate discomfort to the patient, and also continue providing sufficient normal force while the patient moves and the body change shape.

In some embodiments, sensor housing 1602 may contain a transducer array 1602, electronics, including but not limited to a visual display, speakers, and/or battery 1610, and other electronics. In some embodiments, sensor housing 1612 is shaped like a half of an ellipsoid or American football. These shapes were found to be particularly useful in aiding proper positioning and tension characteristics to be applied.

In some embodiments, the sensor housing 1612 may contain a user interface unit 1620, which may be a sensory output device operable with the visual display, speakers, and/or battery 1610. The user interface unit 1620 may function to communicate inputs generated by a user inter-action to the device. For example, the user interface unit 1620 may comprise a sensory output device such as a capacitive touch input device coupled with a visual display 1610. The user interface unit 1620 may function to allow the user to input selections that, when received by the device, cause the device to modify its operation mode (e.g., user input may cause the device to being a process operable to determine a pre-intervention/post-intervention VTI ratio as described below).

In some embodiments, the transducer array 1602 comprises transducer-receiver pairs, where the transducer component generates acoustic waves, transferred into the patient acoustically through a hydrogel or acoustic coupler 1604. The acoustic waves travel through the patient, and are modulated and reflected by media interfaces, for example fluid within a blood vessel. Reflected and modulated waves are sensed by a receiver component in the transducer-receiver pair and within the larger transducer array 1602. In some embodiments, the Doppler shift in a frequency modulated signal generated by the transducer 1602 may provide an accurate representation of the velocity of an element. In some embodiments, the element to be measured is the fluid flow within a blood vessel; non-limiting examples including the carotid artery, the brachial artery, or the femoral artery.

Figure 18:
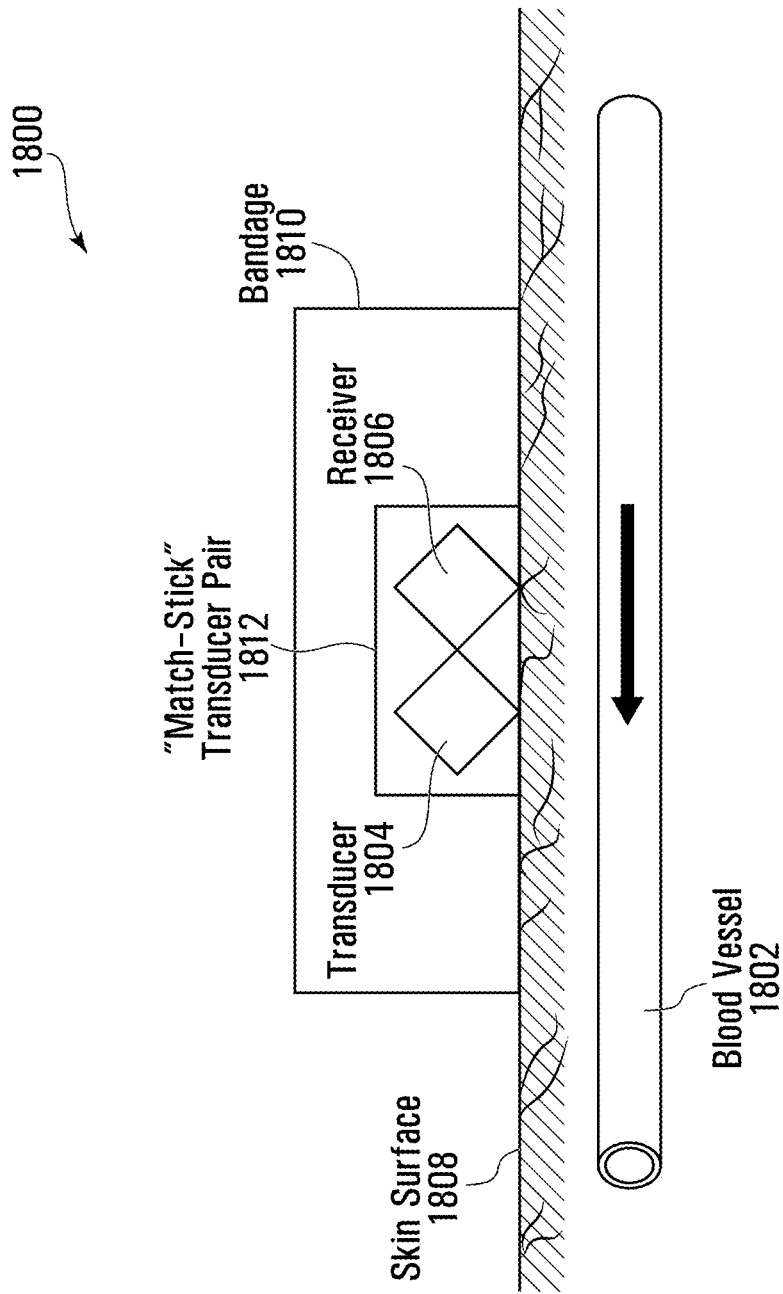
FIG. 18 is a cross-sectional diagram of a device displaying the "saw tooth" configuring of the transducer-receiver pair and its orientation relative to blood vessels, according to some embodiments.
Figure 19:
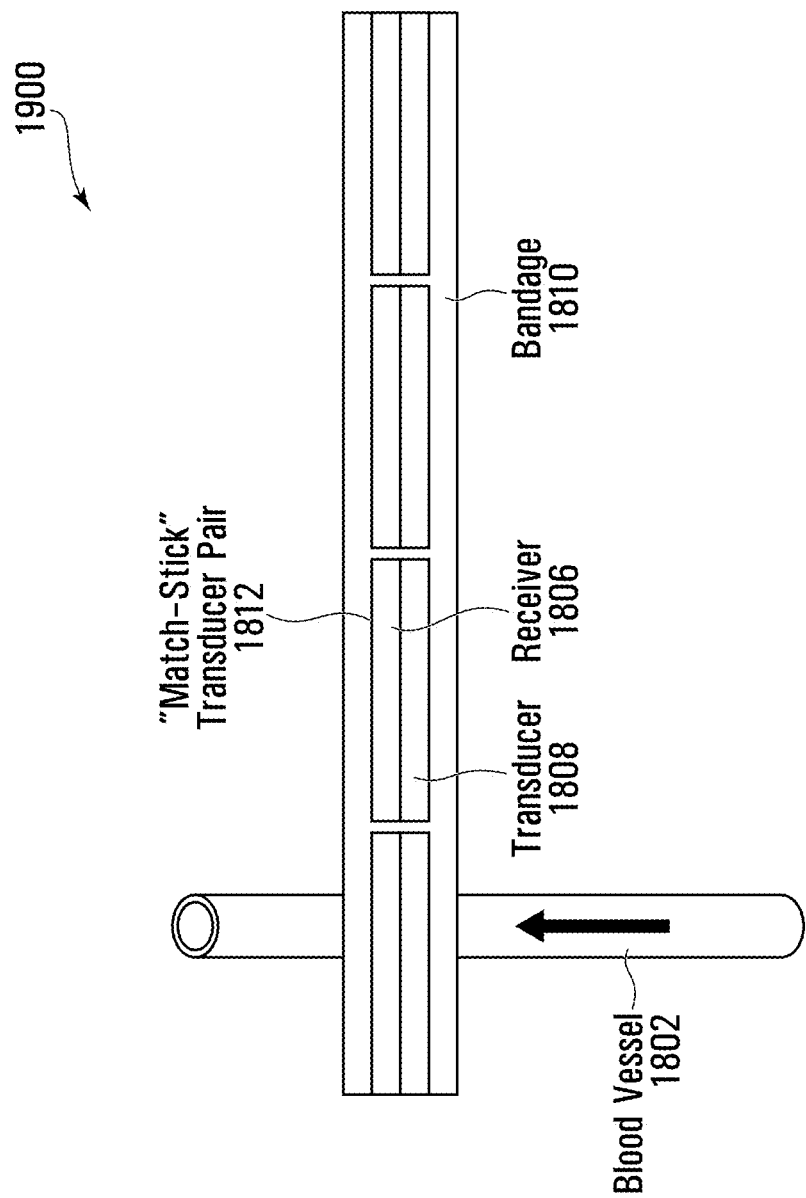
FIG. 19 is a top view diagram of an ultrasound sensor and its orientation elative to blood vessels, according to some embodiments.

According to some embodiments, a sensor consisting of a ultrasound transducer 1804 and receiver 1806 may be configured as depicted in FIG. 18 and FIG. 19, representing a cross-sectional view and an overhead view respectively. Transducer 1804 and Receiver 1806 may be configured such that they parallel to each other, and each directed at a 45 degree angle to the transverse plane (i.e., the plane defined by the surface of the skin 1808 at the local site on the patient). The transducer 1804 and receiver 1806 may resemble two match-sticks, tangent along one edge, as depicted in FIG. 18.

In some embodiments, the orientation of the transducer 1804 and receiver 1806 is configured such that the angle between the vectors defined by the direction of the ultrasound wave and the direction of blood flow is approximately 45 degrees. The transducer pair 1802 can detect blood flow direction by the sign (i.e., positive or negative) of the Doppler shift. The ability to track blood flow direction may aid significantly in diagnosing various ailments or determining whether one or more health-related events have taken place. For example, a change in blood flow direction may indicate that the patient's wound has been successfully sealed, that the patient's circulatory system is working (not working), CPR has been successful, the patient is bleeding out and requires immediate attention, among others.

An increase in frequency (positive shift) indicates blood flowing towards the ultrasound wave generated by the transducer 1804, and vice versa. In some embodiments, the acceptable functional range is about 45-degrees±15-degrees, with 45-degrees representing the preferred embodiment. The reader will understand that in some embodiments, the acceptable functional range may be about 44-degrees±14-degrees, about 46-degrees±16-degrees, etc.

In some embodiments the ultrasound wave (i.e., Doppler beam) is "unfocused"; that is, the beams sweep out an angle of approximately 20-degrees, such that by directing the beam approximately 45-degrees from the transverse plane (as defined by the plane of the skin at the local site), the transducer 1804 will generate a wave that intersects with the blood vessel, and the angle of acceptance of the receiver 1806 (also 20-degrees) is large enough to receive the reflected and modulated signal generated by the blood flow. In this example, the width of the transducer face may be as small as 0.34 mm. This size is suitable for high-frequency (i.e., approximately 7 MHz) applications where high focal loss may be acceptable. Further, the width of the transducer may be as large as 2.15 mm. This size is suitable for low-frequency (i.e., approximately 4 MHz) applications where only low focal loss is acceptable.

In another example, a beam that sweeps out approximately 60-degrees can be constructed. The width of the transducer face may be as small as 0.924 mm. This size is suitable for low-frequency (i.e., approximately 4 MHz) applications where high focal loss may be acceptable. Further, the width of the transducer may be as large as 1.52 mm. This size is suitable for high-frequency (i.e., approximately 7 MHz) applications where only low focal loss is acceptable.

In some embodiments, the functional frequencies of ultrasound waves generated by the transducer 1804 and detectable by the receiver 1806 are approximately 3-8 MHz. In some embodiments, approximately 5 MHz may be the frequency generated by the transducer 1804. Typically, a lower frequency may desirable for larger patients, as vessels such as the carotid artery, femoral artery, brachial artery, etc. are typically further below the skin surface 1808.

The orientation of the "match-stick" configured transducer pair 1802 may, in some embodiments, be fixed relative to the skin surface 1808 by a tensioned bandage 1810 which provides a force normal to the transducer pair 1812 and directed towards the skin surface 1808.

In some embodiments, an audio or visual cue based on the Doppler shift measured by the ultrasound transducer pair 1802 may guide the placement of the device relative to the local site on the patient. A stronger signal relative to the noise sensed by the transducer pair 1802 may be processed by the CPU 604 and outputted to a peripheral speaker or display 606. The output may comprise, for example, a particular sound (e.g. "whoosh"), a change in volume, or frequency of beeps in the case of an audio cue, or it may comprise, for example, brightness, number of LEDs activated, the flashing of a pre-selected image, among others in the case of a visual cue.

In some embodiments, the sensor consists of a "chain" of transducer pairs 1802, as depicted in FIG. 19. Transducer pairs 1802 are mutually connected via co-axial cable. The increased length to the overall sensor increases the acceptable area that the device may be placed by increasing the likelihood that the target blood vessel passes under at least one transducer pair 1802.

In some embodiments, a "chain" may be preferable to a singular, but longer transducer pair 1802, because it may allow the housing to be constructed out of a flexible material that in turn will better conform to the various shapes and sizes of patients. Alternatively, in some embodiments, the transducer may be a flexible polymer transducer (e.g., a highly non-reactive thermoplastic fluoropolymer such as Polyvinylidene difluoride (PVDF)), this may also allow the housing to be constructed out of a flexible material and enable the housing to better conform to patients of various shapes and sizes. Producing the external housing in a flexible fashion may facilitate better acoustic coupling between the device 102 and the body and a higher signal to noise ratio.

Figure 20:
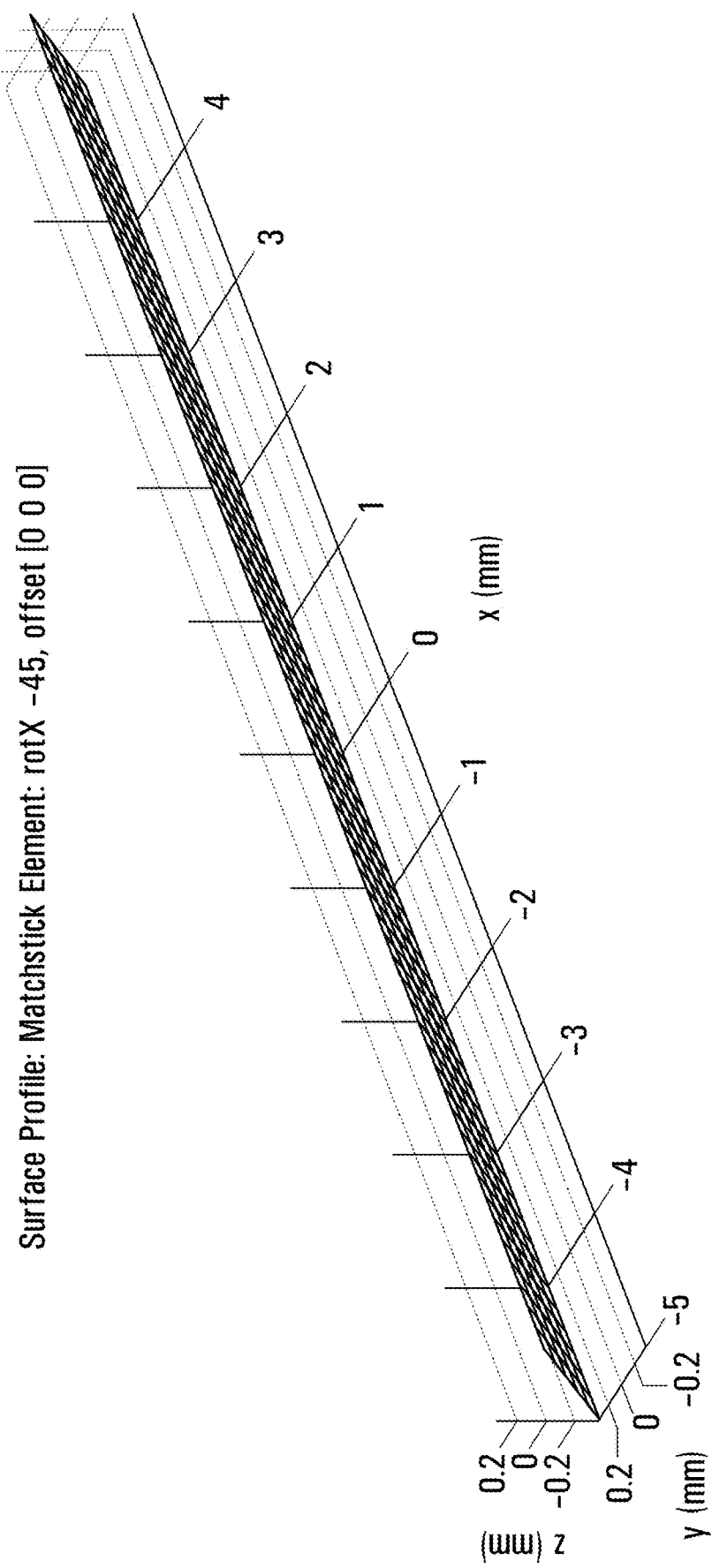
FIG. 20 illustrates an example surface profile of a matchstick element, according to some embodiments.

In some embodiments, the transducer pair 1804 is a piezo-ceramic material. In some embodiments, each piezo ceramic element, representing an individual transducer 1804 or receiver 1806 is 10×1×1 mm in shape. The piezoceramics in some embodiments may be a PZT-5A or PZT-5H or a combination thereof. In some embodiments, the current draw is approximately 25 mAh. In some embodiments, the device may have a mode designed to conserve power and extend battery life. For example, the device may turn on only a pre-set times or it may only turn on at the request of a user and automatically turn off (or "sleep") after a defined period of time. FIG. 20 illustrates an example surface profile of a matchstick element, according to some embodiments.

In some embodiments, the transducer pairs 1804 may be adapted to sense peak velocity of the Doppler Shift, VTI, or the pre-intervention/post-intervention VTI ratio. The device 108 may, according to a pre-programmed instruction set, implement one or more "sampling windows" which may perform a calibration routine functional to eliminate the inherent variability of Doppler signal. The calibration routine may: a) record signals recorded by the transducer pair during a pre-defined span of time prior to the intervention (e.g., 10 seconds) as a "pre-intervention window"; b) cease recording signals during a corresponding pre-defined span of time during the intervention as an "intervention window"; and c) record signals during a corresponding pre-defined span of time subsequent to the intervention as a "post-intervention window".

The VTI is determined, in accordance with a preferred embodiment, based on a based on a baseline sampling prior to intervention. During the time of intervention, various measurements may be taken, in some embodiments. Following intervention, a post-intervention sampling (on the same time period as baseline sample) is determined, and in the preferred embodiment, a VTI ratio is generated pre and post intervention. The VTI determination is a useful, non-invasive technique that, without additional One advantage of the device is the ability to measure both heart rate ("HR") and VTI. This permits the calculation of the HR/VTI ratio—an index that (unlike the Shock Index) is not subject to vascular constriction as a compensatory mechanism during the onset of shock.

In some embodiments, the design, orientation, and frequency of the ultrasonic transducers are specifically designed to facilitate the rapid and repeatable measurement of the signal of interest (e.g., the ultrasonic signal reflected from the vessel of interest).

Subsequently, the measured signal of interest is automatically processed by the signal processing routine in order to generate an output.

Currently available point of care ultrasound machines require several manual steps to be completed in order to return a valid output. Further, successfully completing several of these steps requires users to have specific training and skill. For example, currently available point of care ultrasound machines may require: manual identification of the vessel of interest using an ultrasound imaging screen; manual orientation of the angle of an ultrasound probe in relation to the vessel of interest to produce useful readings; manual identification of the vessel of interest to activate a Doppler function (e.g., a Doppler signal processing function); maintaining a substantially motionless positioning of both the ultrasound probe and the body part containing the vessel of interest; and manually executing a command in order to cause a reading to be taken. Further, often these steps must be executed repeatedly in order to compare changes in outputs received pre and post intervention (e.g., pre and post introduction of a medicament).

In contrast, some embodiments described herein may: automate some or all of the previously described steps; remove or reduce the requirement for manual identification of a vessel of interest; remove or reduce the requirement to manually orientate the ultrasonic transducer(s) relative to the body part of the person containing the vessel of interest; may automate the process of identifying a vessel of interest and activating a Doppler function; may serve to automatically or substantially automatically maintain a substantially motionless positioning of the ultrasonic transducer(s) relative to the vessel of interest; and may automatically generate readings, outputs, and compare pre and post intervention values to measure changes.

Figure 21A:
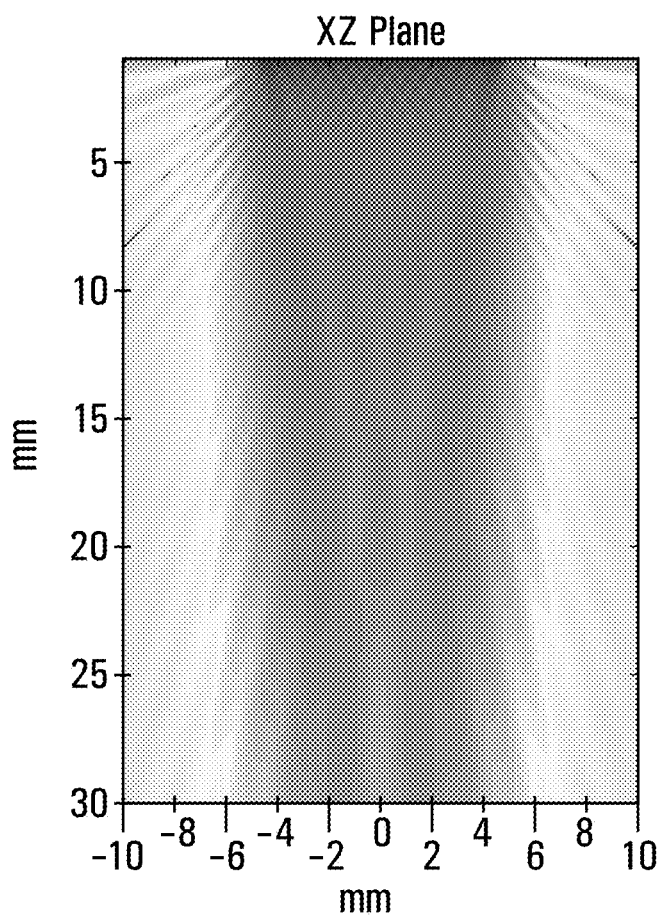
FIG. 21A and FIG. 21B are "heat map" plots of the ultrasonic signals generated by the matchstick transducers, according to some embodiments.
Figure 21B:
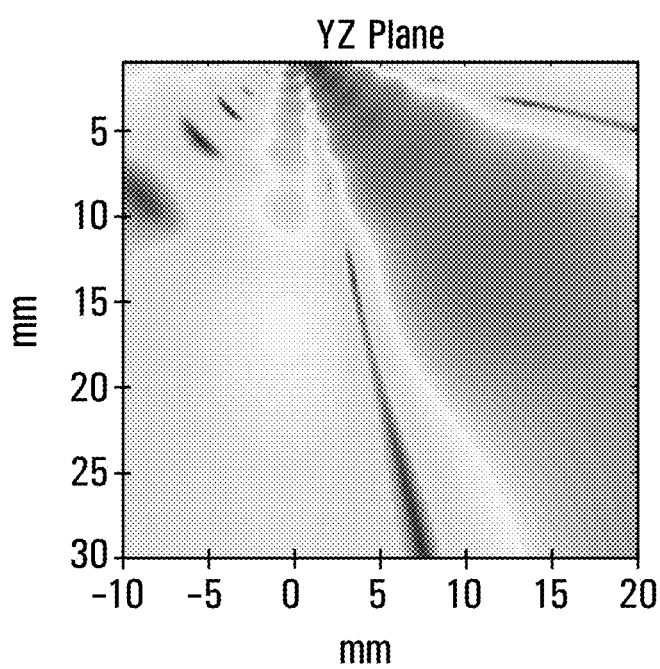

FIG. 21A and FIG. 21B are "heat map" plots of the ultrasonic signals generated by the matchstick transducers, according to some embodiments. FIG. 21A is illustrative of the signal generated in the XZ plane, with the darkness indicative of signal strength. FIG. 21B is illustrative of the signal generated in the YZ plane. As indicated in FIG. 21B, the beam is generated at about 45 degree angle in the YZ plane, and the beam is "wedge"/conical shaped. A conical shape, for example, may include an oval cone, and in some embodiments, may be frusto-conical.

Figure 21C:
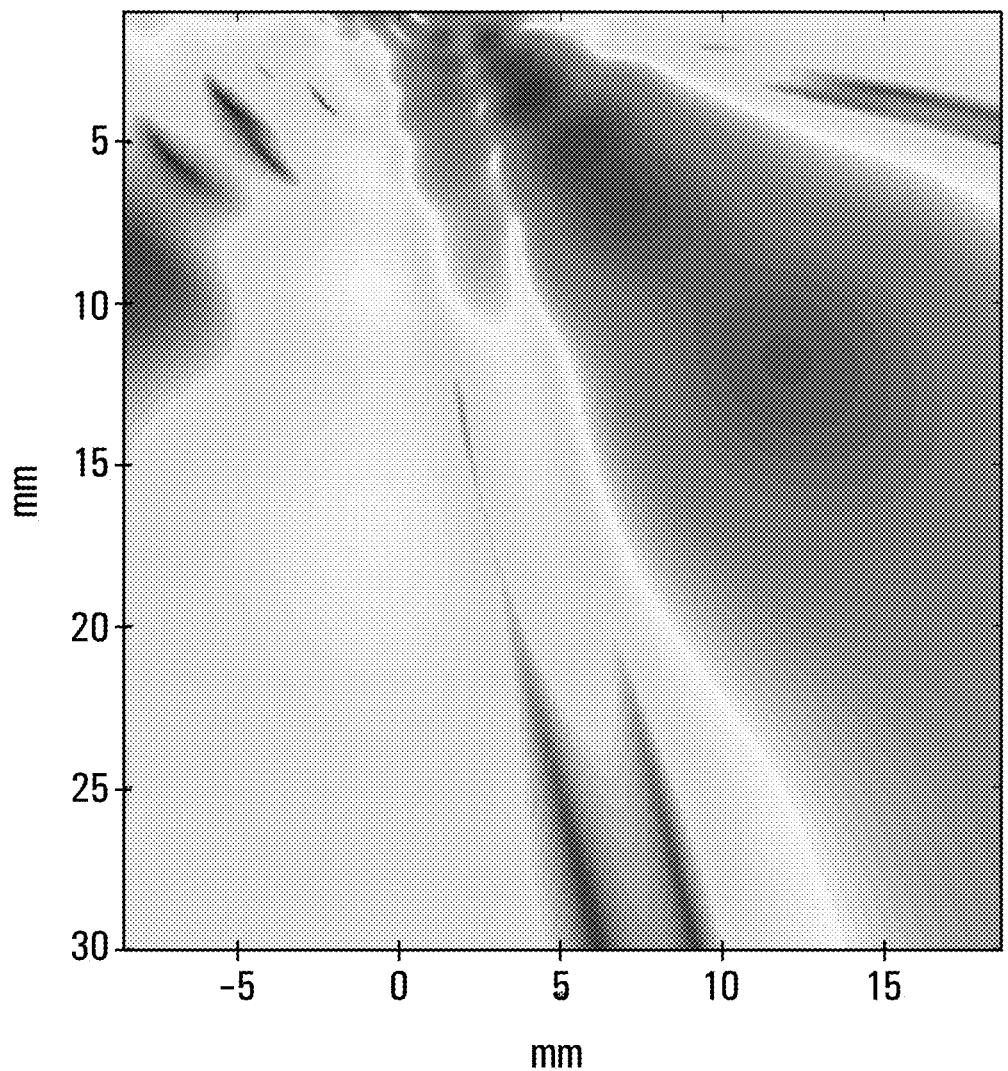
FIG. 21C is a more detailed version of FIG. 20B, showing the beam "wedge" in greater detail.

FIG. 21C is a more detailed version of FIG. 20B, showing the beam "wedge" in greater detail. In FIG. 21C, the relative signal strength is shown at 3 MHz for a matchstick transducer having the dimensions of 10×1 mm, spaced at 3 mm.

Figure 22:
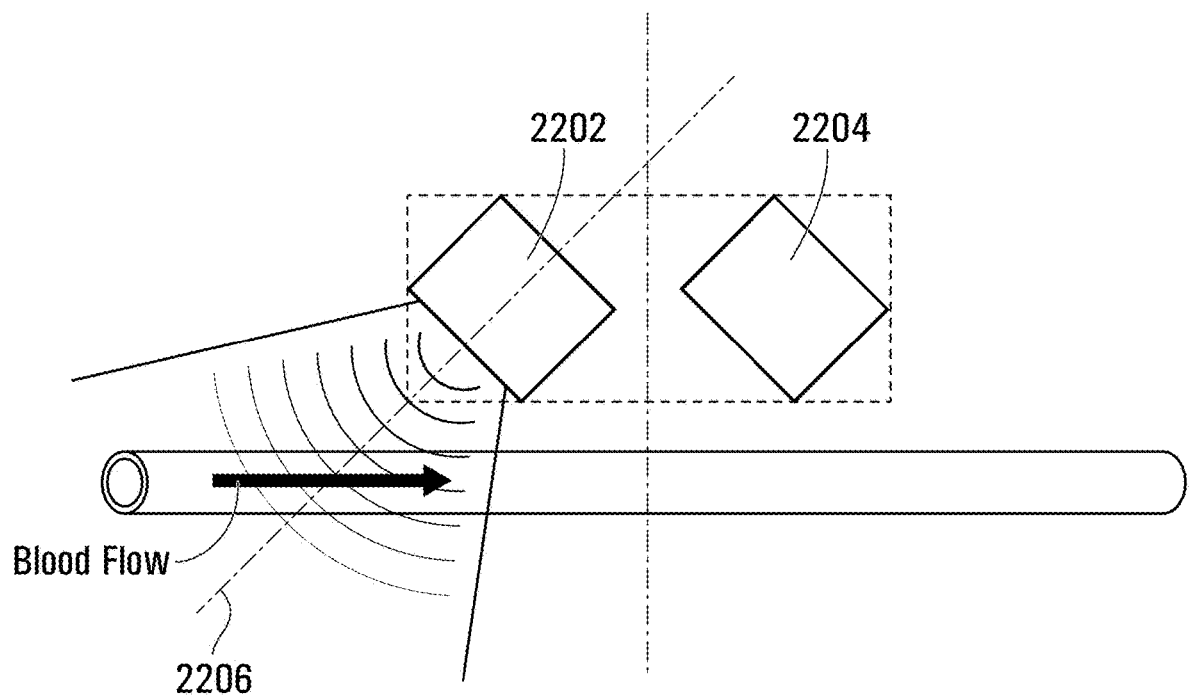
FIG. 22 illustrates two matchstick elements and a blood vessel of interest, according to some embodiments.

FIG. 22 illustrates two matchstick elements and a blood vessel of interest, according to some embodiments. In this example, a first matchstick element 2202 provides a signal transmit function whereby the ultrasound signal is generated in a wedge shape towards the blood vessel 2206, for example, along center axis 2208. A second matchstick element 2204 is configured to receive the signal that is reflected from blood vessel 2206. The orientation is important in some embodiments, the first matchstick element 2202 is positioned in front of the second matchstick element 2204 such that the signal emanating from first matchstick element 2202 is not inadvertently impeded by the second matchstick element 2204. Accordingly, in some embodiments, there may be some directionality related to the positioning of the device for proper functioning (while the device provides a wide latitude of redundant angles and positioning, to get a sufficiently strong signal reading, the device may need to be oriented at least roughly in the correct direction). Accordingly, there may be a rough "up" and "down' direction associated with the device, but the configuration of the matchstick transducers and additional elements allow for a wide range of variation in orientations and positioning.

Figure 23:
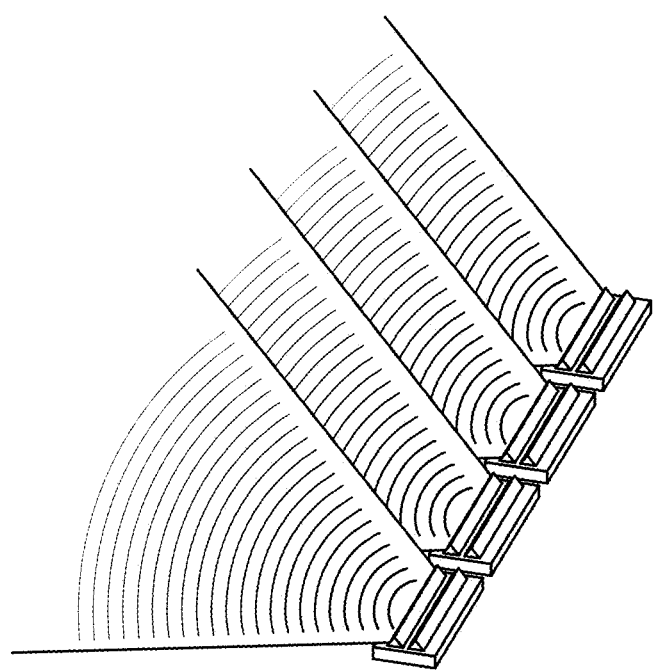
FIG. 23 illustrates a series of matchstick transducer pairs, according to some embodiments.

FIG. 23 illustrates a series of matchstick transducer pairs, according to some embodiments. In FIG. 23, the plurality of matchstick transducer pairs 2302, 2304, 2306, and 2308, in combination/in concert, provide an "unfocused curtain" 2310 of signal, all at or around the same angle relative to the matchstick transducer pairs 2302, 2304, 2306, and 2308. While there may be some slight differences in angles between each of the transducer pairs 2302, 2304, 2306, and 2308, for example, due to the device flexing to conform to the anatomy of an individual (e.g., if the spacing between the transducer pairs 2302, 2304, 2306, and 2308 is a flexible material), the angles are fairly constant and are not used to focus the beams together.

Rather, the unfocused curtain 2310 of signal formed by the substantially conical/frusto-conical (e.g., "wedge" shaped) signals generated causes a plurality of different reflections and signals to be received by the receiving transducers of each of the transducer pairs transducer pairs 2302, 2304, 2306, and 2308. The receiving members of the transducer pairs, in some embodiments, do not discriminate between signals of the transmitting transducer members, and accordingly, an improved signal strength (and/or improved signal to noise ratio) is possible.

The unfocused curtain 2310 generated by the plurality of transducer members generating signals increases the breadth of different angles of placement that still render a sufficiently strong received signal indicative of blood flow. For example, for a device that is haphazardly placed on an injured person in an emergency situation, reflections may be identified at differing angles from each of the transducer signal transmitting members, each having different strengths. Each of the signal receiver members may receive signals of different amplitudes and frequencies that may be indicative of blood flow across the vessel of interest, and in some embodiments, the device is configured to select and process signals from a subset of signal receiver members (e.g., only those signal receiver members receiving the strongest signals). Accordingly, the device has increased flexibility in placement, and there is no need for accurate landmarking of anatomical elements or careful positioning or placement as the unfocused curtain 2310 increases the probability that at least one of the "wedges" is able to intersect the blood vessel such that a sufficiently strong signal can be received by one of the signal receiver members.

Figure 24:
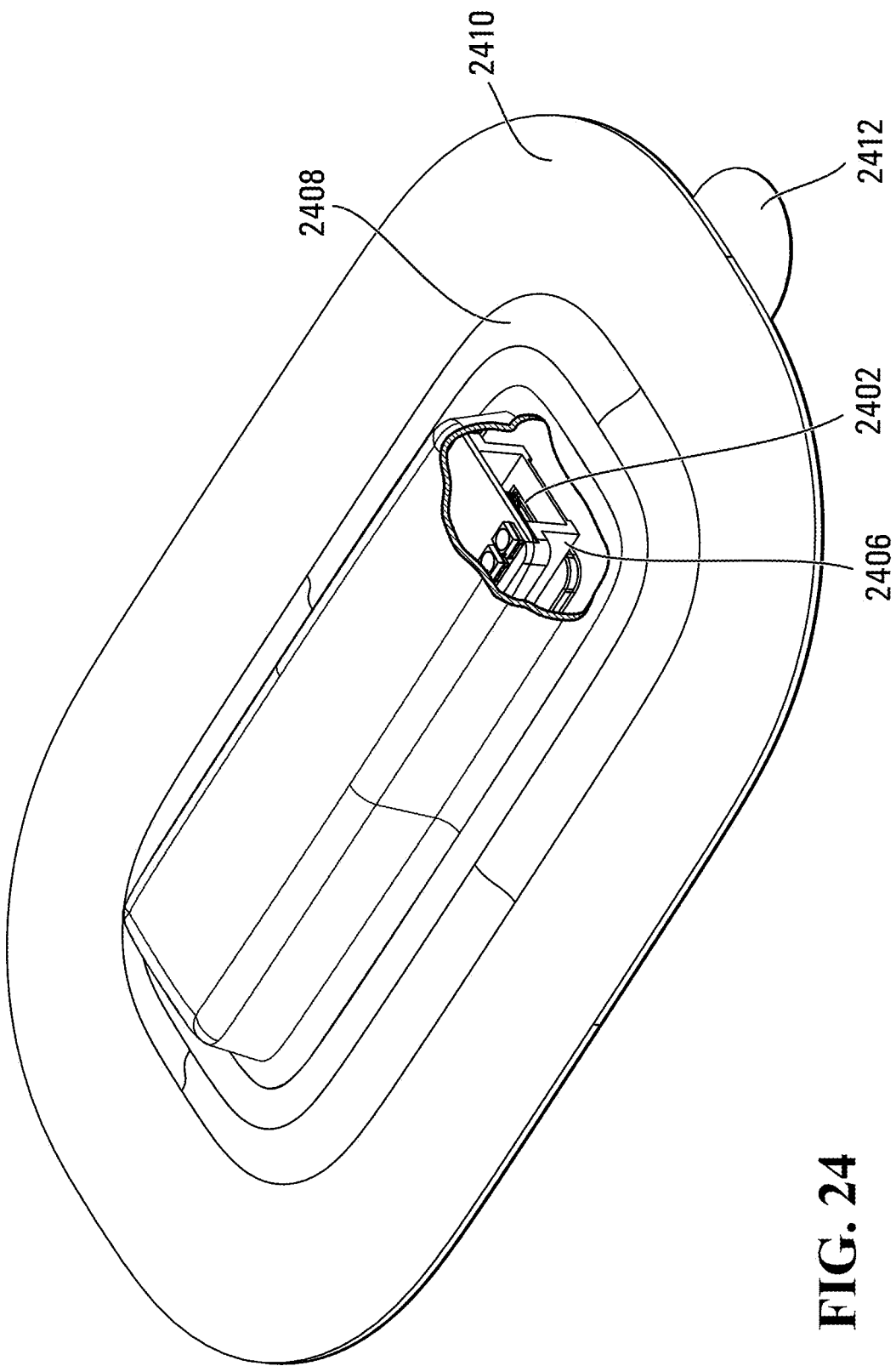
FIG. 24 is a perspective rendering of a device, according to some embodiments.

FIG. 24 is a perspective rendering of a device, according to some embodiments. The device shown in FIG. 24 is shown as a non-limiting example of a physical device, and includes a set of piezo-electric crystal transducer pairs encased in an injection molded crystal retainer housing. Each pair may have its own housing, and in this example, each retainer housing is provided on a flexible circuit (e.g., for providing electrical connectivity between the pairs), that is coupled to an energy storage device (e.g., a battery, a capacitor).

The flexible circuit may be disposed on a printed circuit board 2402, which is then provided within an injection molded rigid chassis 2406. Flexible urethane pads may be used to provide comfortable coupling when pressed against the skin of a user, and the entirety of the device may be housed within a silicon over-mold 2408 that is shaped as an adhesive bandage 2410 having a hydrogel insert to aid in the dispersion of signal into the body. The device may ultimately be placed on a backing paper 2412 having an adhesive for application onto the body. The device may include on-board processors and memory, which receive and process/pre-process the signals received by the receiving elements of the transducers.

These signals may be transmitted to downstream components for further processing, which in some embodiments, are remote from the device (e.g., a smartphone, a computer, a tablet). In other embodiments, an on-board display or interface elements are disposed on or within the housing such that various alarms and notifications may be generated based on the processed signals. For example, the alarms and notifications may indicate a quality of treatment and indicate to an emergency responder whether treatment is effective or is failing, based on determinations obtained from the processing signals, such as determined HR/VTI ratios, among others.

Figure 25:
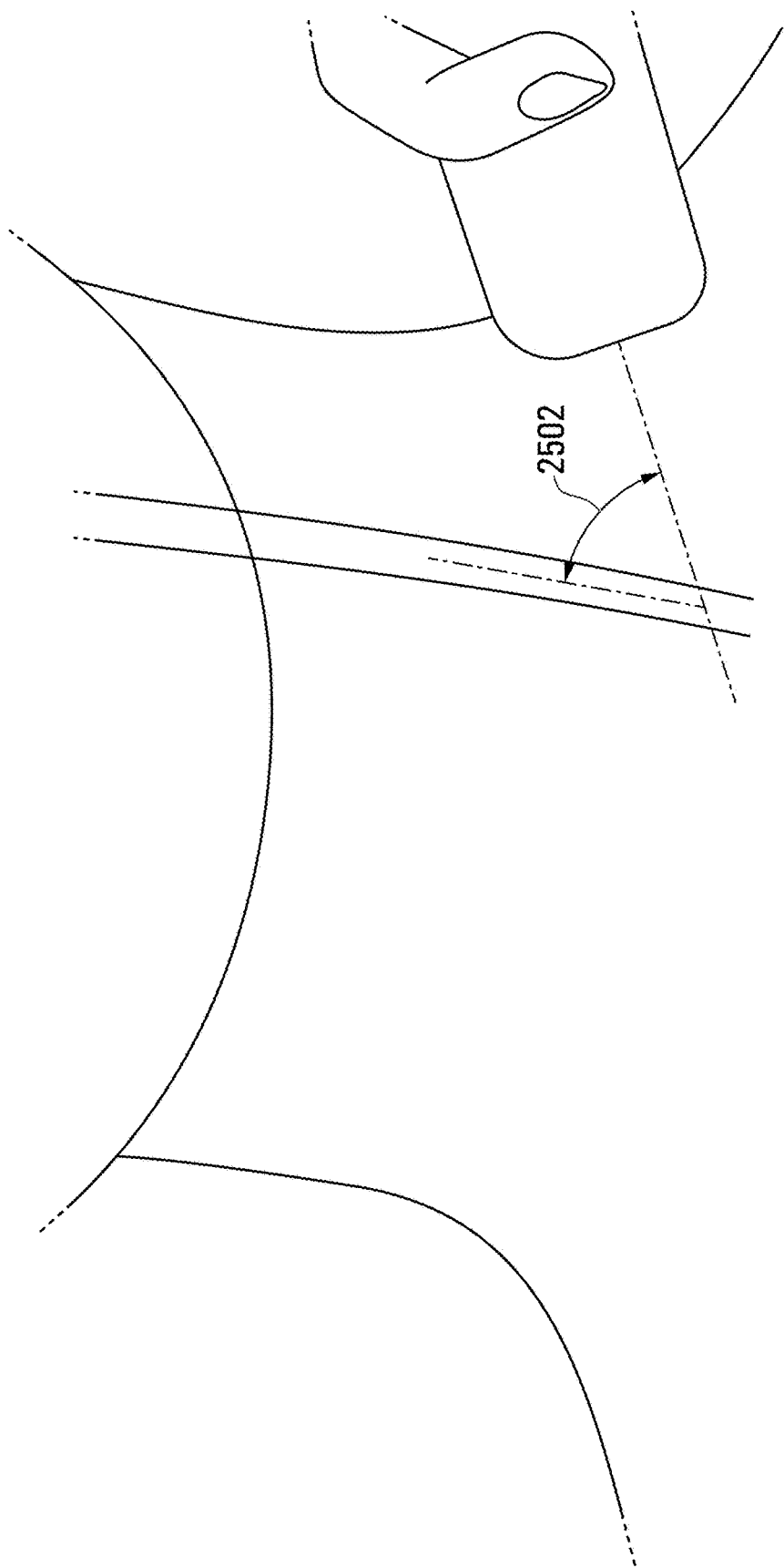
FIG. 25 is an illustrating indicating an approach to obtaining measurements and signals using a typical handheld device.

FIG. 25 is an illustrating indicating an approach to obtaining measurements and signals using a typical handheld device. In FIG. 25, it is important to note that the required angle 2502 necessarily needs to be very precise, otherwise a sufficient measurement is not obtained.

Figure 27:
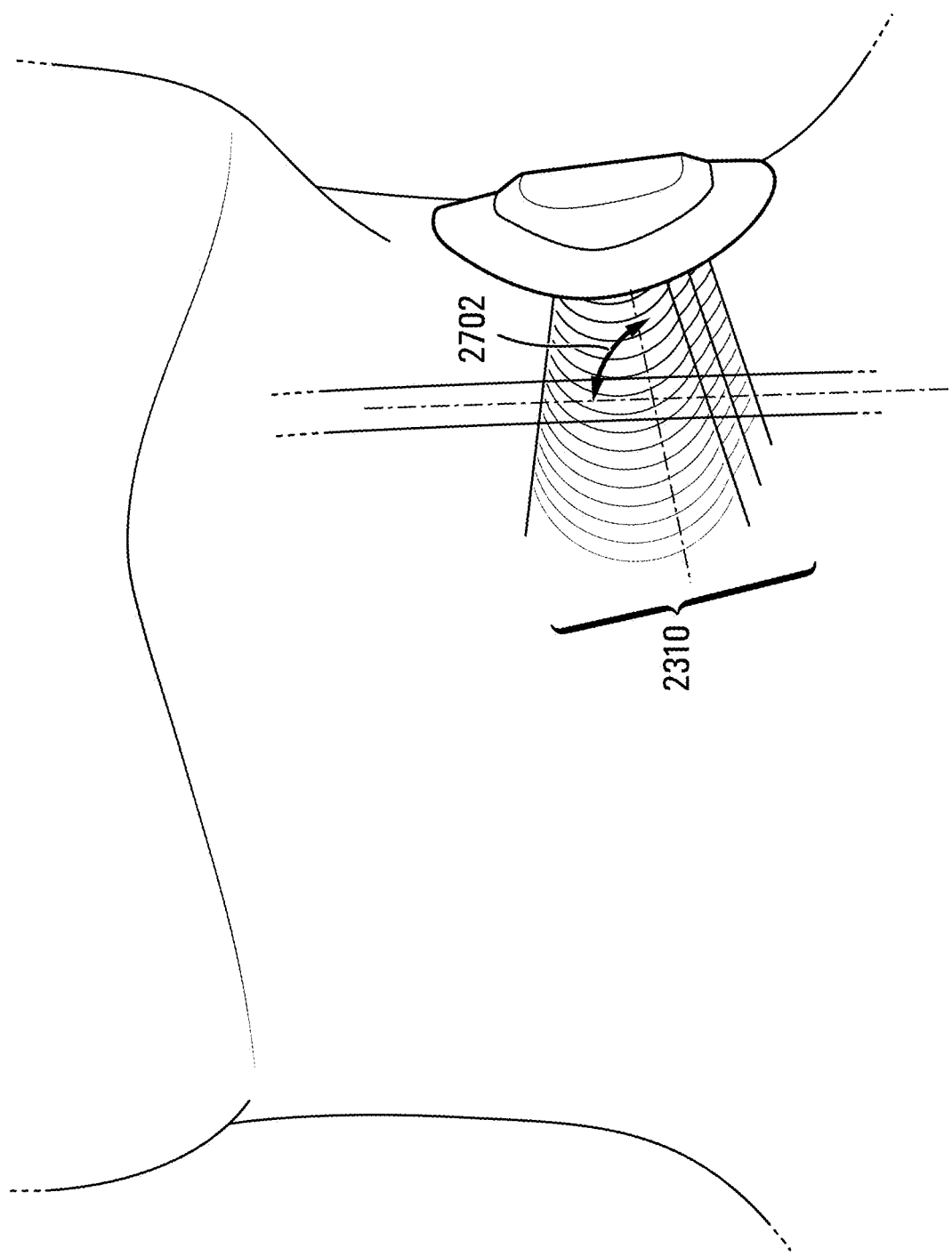

In FIGS. 26 and 27, a device providing an unfocused curtain 2310 is provided, according to some embodiments. The device does not need to be precisely positioned on the user, and the plurality of matchstick pairs of transducers allow for a plurality of "wedge shaped" signals to be transmitted, the angles being generally consistent except for differing angles due to the bandage conforming to the form of the neck of the user. Accordingly, the probability of the device obtaining sufficiently strong signals in return is significantly increased relative to the device of FIG. 25, allowing for a redundancy of placement options and orientations.

The "unfocused" aspect of the curtain of ultrasound signal improves the usefulness of the example device of FIGS. 26 and 27 relative to the device of FIG. 25 in emergency situations. An unskilled or relatively less skilled user would more readily be able to use the device to achieve a desired healthcare outcome of obtaining measurements and insights based on blood flow characteristics of blood flow through the vessel of interest. In FIG. 27, while the signals of one of the pairs of transducers on the device intersect the blood vessel at a 60 degree angle, the other pairs may generate signals that intersect the blood vessel at different angles (e.g., 50 degrees, 45 degrees, 65 degrees, 70 degrees), and the receiving elements obtain an improved signal. In some embodiments, the device is further configured to select a subset of receiving elements that have signals greater than a particular threshold (or to simply pick the highest signal or the cleanest signal)

Figure 28:
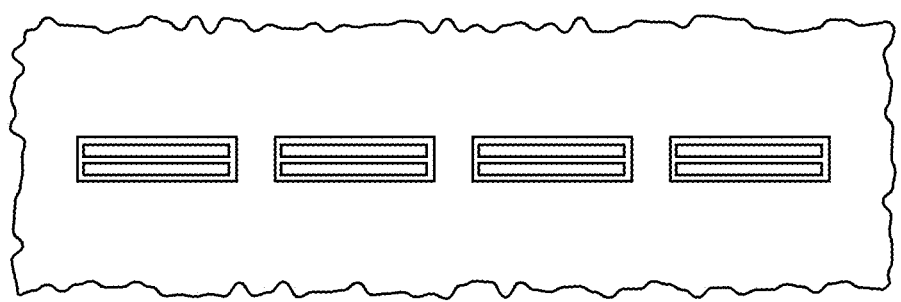
FIG. 28 is a photograph of a set of matchstick transducers, according to some embodiments.

FIG. 28 is a photograph of a set of matchstick transducers, according to some embodiments. The transducers are shown as examples, and variations are possible. In the photographed example, the geometries of the transducers are 1 mm×1 mm×10 mm in a four pair set oriented tip to tail.

The transducers, in combination, to create a long and flexible transducer that produces signals in a saw tooth orientation (e.g., similar to a matchstick on edge). Transducers can be embedded in a flexible housing to enable the transducer to flex and effectively couple to the skin.

In a non-limiting example of a method of use, the orientation of the transducer is placed across the neck (parallel to collar bone). Positioning the transducers in this orientation is found to increase the probability of intersecting the carotid and jugular, without the need for landmarking or focusing ultrasound beams on the carotid, as required in conventional approaches.

The device may be of various shapes, dimensions, and sizes, and in a preferred embodiment, a length of device is about 45 mm, and the transducer elements (e.g., transmitting elements) are spaced apart from one another, while having generally the same angle (that may shift slightly as the device conforms to a patient's body part).

Tight spacing is a consideration in relation to near field sensitivity—the spacing between elements provides for overlap between the transmission and receiving signal fields. In various embodiments, the spacing of individual transmitting element to other transmitting elements is less than about 1 mm, less than about 2 mm, less than about 3 mm, or less than about 4 mm, and the spacing must be less than 5 mm.

In an illustrative example, the geometry of an array may include the following: element (10 mm)—gap (1-5 mm)—element (10 mm)—gap (1-5 mm)—element, etc. Similarly, the spacing of a transmitting array to a receiving array is less than about 1 mm, less than about 2 mm, less than about 3 mm, or less than about 4 mm, and the spacing must be less than 5 mm.

Since the range to near field targets is fairly small (10-20 mm), the attenuation of the Doppler signal will be also quite low, and some attenuation of the Rx signal may be permissible due to non-overlap with the Tx beam (Round Trip sensitivity loss at near field depths). For example, a reduction in near field Rx sensitivity due to non-overlap of 20 dB may be acceptable, in some cases. In other words, the receiving signal could be 20 dB weaker than an optimally aligned near field geometry, and the device of some embodiments would still be operable.

Impedances can be selected to modify performance characteristics of the device. In experimentation, Applicants were able to obtain sufficient penetration with a 40 ohm real part impedance and single ended transmission driver.

In other embodiments, the device is adapted to increase the drive amplitude by a multiple of 2 by using a differential driver architecture, implying that the device is able to achieve good performance for impedances at high as 80 ohms real part impedance, for the full transmitter array, all elements oriented in an electrical parallel connection.

In some embodiments, the transducers are selected to have an impedance specification of between 30 ohms and 100 ohms real part. In some embodiments, the system includes a series tuning inductor configured to tune out the series capacitance.

With respect to the receiver elements, the receiver elements are driven into a high load impedance (>=1 K ohm), so the element impedance is relatively immaterial, and accordingly, receiver source impedance <about 200 ohms may be appropriate, in some embodiments.

A working depth of about 1-6 cm is provided, according to some embodiments. At the shallow depth, the attenuation of the Doppler signal will be very low, and in some embodiments, a poor overlap of Tx and Rx beams can be thus tolerated. For example, a 20 dB reduction in round trip sensitivity from targets on the nominal "center" of the beam could be allowable without significant impact of the Doppler performance.

In another embodiment, the device is skewed for improved sensitivity in the 3-6 cm depth range, and with a tradeoff in performance in the near field.

In Applicants' experiments, in the lateral dimension (45 mm nominal) the beam was found to have a basically Rectangular shape, providing essentially a sheet of ultrasound energy. In an elevation dimension (1 mm nominal), the beam was found to have some focusing, with a beamwidth of 20-30 degrees, allowing the thickness of the "sheet" of ultrasound energy to be set.

In a situation where the device is used to interrogate the target vessel at an angle of 45 degrees nominal, a −3 dB total beamwidth of 20 degrees may cause some variance in the Doppler velocity, potentially in the range of +−15%. For a 30 degree beamwidth, the Doppler velocity variance will be about +/−20%, and Applicants' testing have indicated that a beamwidth of <30 degrees@−3 dB may be required for some embodiments.

Figure 29:
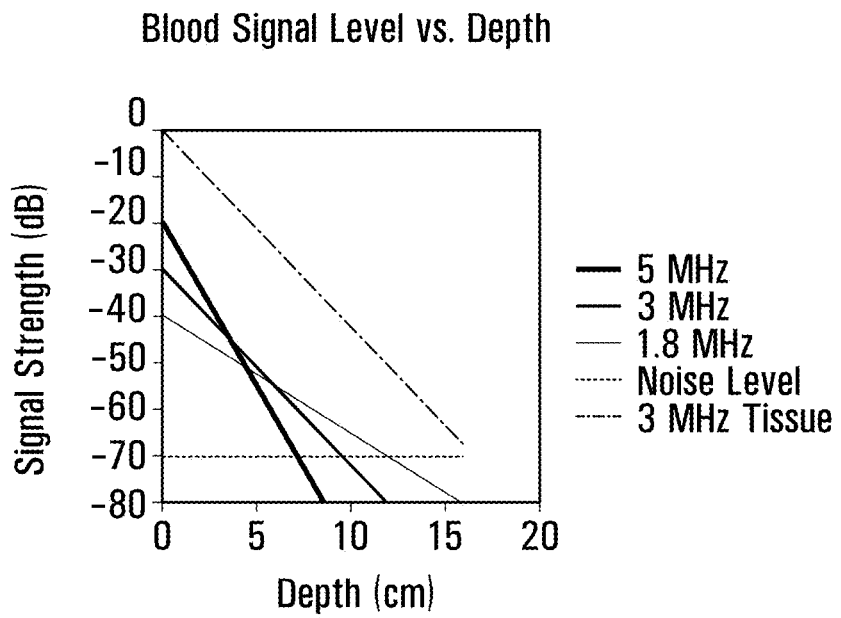
FIG. 29 is an illustrative graph of blood signal level as compared to depth, according to some embodiments.

In selecting operative frequencies, Applicants have identified that about 3-8 MHz frequency is operable, and 4-5 MHz is preferred. Experiment approaches have indicated that the signal is sufficient that the transducer pairs can be wired in parallel, and FIG. 29 is provided as an illustrative graph of blood signal level as compared to depth, according to some embodiments.

Figure 30:
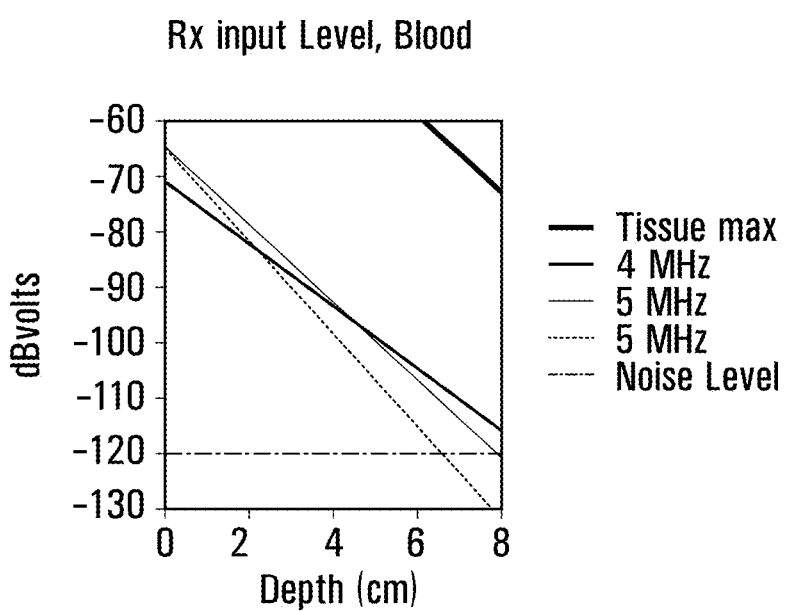
FIG. 30 is a graph illustrating received signal input level, in blood, showing dBvolts plotted against depth, in centimeters.

In some situations, there may be requirements to obtain deep tissue readings (e.g., >4 cm about below the surface) as many critically ill patients have very large necks due to high body mass index. For example, where deep tissue readings are required, the dimensions and geometry of the device and/or transducers are modified to enable a deeper ultrasound curtain (e.g., for bariatric patients that are greater than 500 lbs). FIG. 30 is a graph illustrating received signal input level, in blood, showing dBvolts plotted against depth, in centimeters.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more sensory output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references is be made regarding servers, services, interfaces, platforms, or other systems formed from computing devices.

It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The embodiments described herein are also implemented by physical hardware, including computing devices, servers, receivers, transmitters, processors, memory, displays, and networks. The embodiments described herein provide useful physical machines and particularly configured computer hardware arrangements.

The embodiments described herein are also directed to electronic machines and methods implemented by electronic machines adapted for processing and transforming ultrasonic signals which represent various types of information. The embodiments described herein pervasively and integrally relate to machines, and their uses; and the embodiments described herein have no meaning or practical applicability outside their use with computer hardware, machines, and various hardware components.

Substituting the physical hardware particularly configured to implement various acts for non-physical hardware, using mental steps for example, may substantially affect the way the embodiments work. Such hardware limitations are clearly essential elements of the embodiments described herein, and they cannot be omitted or substituted for mental means without having a material effect on the operation and structure of the embodiments described herein. The hardware is essential to implement the various embodiments described herein and is not merely used to perform steps expeditiously and in an efficient manner. In some embodiments, the device is a single or special purpose machine that is specifically designed to perform limited set of functionality.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized.

As can be understood, the examples described above and illustrated are intended to be exemplary only.

What is claimed is:

1. A portable non-invasive hemodynamic monitoring device comprising:
    a housing configured for removable coupling to a body part of an individual, the body part including at least one vessel of interest;
    an ultrasound unit coupled to the housing and adapted for adducing ultrasonic waves into the at least one vessel of interest in a continuous wave transmission, the ultrasound unit including:
        a plurality of transducer pairs adapted to transmit the continuous wave transmission with a first transducer in each of the plurality of transducer pairs and continuously detect reflected ultrasonic waves with a second transducer in each of the plurality of transducer pairs, the reflected ultrasonic waves derived at least in part from the produced ultrasonic waves directed at the at least one vessel of interest and oriented such that, in concert, the plurality of transducer pairs produce the ultrasonic waves at an angle of incidence between about 25 degrees to about 60 degrees in respect of a plane of fluid flow through the at least one vessel of interest;
    a processor configured to continuously extract hemodynamic parameters from one or more characteristics of the detected reflected ultrasonic waves in real-time or near real-time by applying a signal processing routine before, during, and after an intervention while the housing remains coupled to the body part, and to store the extracted one or more hemodynamic parameters in a data storage, the hemodynamic parameters including at least a velocity-time integral (VTI) of signal changes between heartbeats, and a ratio measured between a post-intervention VTI and a pre-intervention VTI; and
    a sensory output device adapted to provide feedback based at least on the extracted hemodynamic parameters and the ratio between the post-intervention VTI and the pre-intervention VTI, the sensory output device including at least one of (i) a graphical display and (ii) an auditory display;
    wherein the orientation of the plurality of transducer pairs is maintained by the housing such that the plurality of transducer pairs are oriented to adduce the ultrasonic waves at substantially similar angles in respect of the plane of fluid flow through the at least one vessel of interest, the ultrasonic waves in concert defining an unfocused ultrasonic curtain that enables a plurality of redundant effective placement positions of the portable non-invasive hemodynamic monitoring device.

2. The portable non-invasive hemodynamic monitoring device of claim 1, wherein the hemodynamic parameters are extracted across multiple distinct events, the multiple distinct events including at least one type of event selected from a chest compression, surgical interventions, catheter-based interventions, a fluid challenge, a passive leg raise, a change in ventilator setting, and an administration of medication.

3. The portable non-invasive hemodynamic monitoring device of claim 1, wherein the first transducer is a signal generation transducer and the second transducer is a signal receiving transducer, and the signal generation transducer of each transducer pair is configured to be positioned proximal to the at least one vessel of interest relative to the signal receiving transducer of each transducer pair.

4. The portable non-invasive hemodynamic monitoring device of claim 1, wherein each of the angles of incidence of the produced ultrasonic waves generated by each transducer pair of the plurality of transducer pairs are substantially similar, after accounting for variations resulting from the portable non-invasive hemodynamic monitoring device conforming to the body part of the individual.

5. The portable non-invasive hemodynamic monitoring device of claim 1, wherein the plurality of transducer pairs is at least one of: a flexible polymer based transducer pair, a piezo ceramic based transducer pair, and a composite based transducer pair.

6. The portable non-invasive hemodynamic monitoring device of claim 1, wherein each transducer pair of the plurality of transducer pairs is configured to generate a substantially conical signal, the plurality of transducer pairs, in concert, generating a plurality of substantially conical signals having the substantially similar angles of incidence, the plurality of substantially conical signals defining the unfocused ultrasonic curtain.

7. The portable non-invasive hemodynamic monitoring device of claim 1,
wherein the processor is further configured to detect an estimated return of spontaneous circulation (ROSC) event by measuring a difference between a first relative blood flow from a chest compression and a second relative blood flow from a heartbeat; and
the sensory output device is configured to generate a sensory output indicating the occurrence of the detected estimated ROSC event and indicating that chest compression activities should cease;
wherein the ROSC event is detected by identifying a predefined number of indicative waveforms that are either out of synchronicity or occur out of phase in relation to the chest compressions activities being administered to the individual.

8. The portable non-invasive hemodynamic monitoring device of claim 1, wherein the sensory output device is configured to generate one or more alarm notifications in response to the ratio exceeding a pre-defined threshold.

9. The portable non-invasive hemodynamic monitoring device of claim 1, wherein the frequency of the ultrasonic waves is a frequency selected from a range from about 3 MHz to about 6 MHz.

10. The portable non-invasive hemodynamic monitoring device of claim 1, wherein the processor is further configured to determine whether the individual is undergoing compensated shock by:
continuously monitoring a second ratio between a heart rate and the VTI of fluid flow through the at least one vessel of interest;
entering a compensated shock alarm state when the second ratio exceeds a pre-defined threshold; and
producing an alarm signal when the compensated shock alarm state is entered.

11. A method for portable hemodynamic monitoring, the method comprising:
coupling an ultrasound unit to a body part of an individual, the body part including at least one vessel of interest;
adducing, by the ultrasound unit, ultrasonic waves into the at least one vessel of interest in a continuous wave transmission, the ultrasound unit including:
a plurality of transducer pairs that each include a signal generation transducer transmitting the continuous wave transmission and a signal receiving transducer, at least a portion of the signal receiving transducers adapted to continuously detect reflected ultrasonic waves derived at least in part from the produced ultrasonic waves directed at the at least one vessel of interest and oriented such that, in concert, the plurality of transducer pairs produce the ultrasonic waves at an angle of incidence between about 25 degrees to about 60 degrees in respect of a plane of fluid flow through the at least one vessel of interest;
continuously extracting hemodynamic parameters from one or more characteristics of the detected reflected ultrasonic waves in real-time or near real-time by applying a signal processing routine before, during, and after an intervention while the ultrasound unit remains coupled to the body part, the hemodynamic parameters including at least a velocity-time integral (VTI) of signal changes between heartbeats, and a ratio measured between a post-intervention VTI and a pre-intervention VTI;
storing the extracted hemodynamic parameters in a data storage device; and
generating sensory outputs providing feedback based at least on the extracted hemodynamic parameters;
wherein the orientation of the plurality of transducer pairs is maintained such that the plurality of transducer pairs are oriented to adduce the ultrasonic waves at substantially similar angles in respect of the plane of fluid flow through the at least one vessel of interest, the ultrasonic waves in concert defining an unfocused ultrasonic curtain that enables a plurality of redundant effective placement positions of the portable non-invasive hemodynamic monitoring device.

12. The method of claim 11, wherein the hemodynamic parameters are extracted across multiple distinct events, the multiple distinct events including at least one type of event selected from a chest compression, surgical interventions, catheter-based interventions, a fluid challenge, a passive leg raise, a change in ventilator setting, and an administration of medication.

13. The method of claim 11, wherein the signal generation transducer of each transducer pair is configured to be positioned proximal to the at least one vessel of interest relative to the signal receiving transducer of each transducer pair.

14. The method of claim 11, wherein each of the angles of incidence of the produced ultrasonic waves generated by each transducer pair of the plurality of transducer pairs are substantially similar, after accounting for variations resulting from the portable non-invasive hemodynamic monitoring device conforming to the body part of the individual.

15. The method of claim 11, wherein the plurality of transducer pairs includes at least one of: a flexible polymer based transducer pair, a piezo ceramic based transducer pair, and a composite based transducer pair.

16. The method of claim 11, wherein each transducer pair of the plurality of transducer pairs is configured generate a substantially conical signal, the plurality of transducer pairs, in concert, generating a plurality of substantially conical signals having substantially similar angles of incidence, the plurality of substantially conical signals defining the unfocused ultrasonic curtain.

17. The method of claim 11, wherein the processor is further configured to detect an estimated return of spontaneous circulation (ROSC) event by measuring a difference between a first relative blood flow from a chest compression and a second relative blood flow from a heartbeat;
    wherein the sensory outputs are adapted for indicating the occurrence of the detected estimated ROSC event and indicating that chest compression activities should cease; and
    wherein the ROSC event is detected by identifying a predefined number of shark-fin shaped waveforms that are either out of synchronicity or occur out of phase in relation to the chest compressions activities being administered to the individual.

18. The method of claim 11, further comprising generating one or more alarm notifications in response to the ratio exceeding a pre-defined threshold.

19. The method of claim 11, wherein the frequency of the ultrasonic waves is a frequency selected from a range from about 3 MHz to about 6 MHz.

20. The method of claim 11, wherein the processor is configured to determine whether the individual is undergoing compensated shock by: continuously monitoring a ratio between a heart rate and a velocity-time integral of fluid flow through the at least one vessel of interest; entering a compensated shock alarm state when the ratio exceeds a pre-defined threshold; and producing an alarm signal when the compensated shock alarm state is entered.

\* \* \* \* \*